(12) United States Patent
Schaffer

(10) Patent No.: US 7,624,864 B1
(45) Date of Patent: Dec. 1, 2009

(54) PERMANENT SHARPS CAPTURE DEVICES, SYSTEMS AND METHODS OF USE

(75) Inventor: Michael Schaffer, Coral Springs, FL (US)

(73) Assignee: Medvision, Inc., Cary, NC (US)

( * ) Notice: Subject to any disclaimer, the term of this patent is extended or adjusted under 35 U.S.C. 154(b) by 66 days.

(21) Appl. No.: 11/765,682

(22) Filed: Jun. 20, 2007

Related U.S. Application Data

(63) Continuation of application No. 11/399,201, filed on Apr. 6, 2006.

(60) Provisional application No. 60/669,539, filed on Apr. 8, 2005, provisional application No. 60/819,453, filed on Jul. 7, 2006.

(51) Int. Cl.
*B65D 85/24* (2006.01)

(52) U.S. Cl. .................. 206/363; 206/365; 220/825

(58) Field of Classification Search ......... 206/363–366; 220/825–826, 837, 839, 916; 229/120.03, 229/121, 122.2
See application file for complete search history.

(56) References Cited

U.S. PATENT DOCUMENTS

| | | | | |
|---|---|---|---|---|
| 4,120,420 A | * | 10/1978 | Dirksing | ............. 229/117.3 |
| 5,145,063 A | * | 9/1992 | Lee | .................. 206/364 |
| 5,284,291 A | * | 2/1994 | Sellors | ............. 229/120.03 |
| 5,322,165 A | | 6/1994 | Melker et al. | |
| 5,395,338 A | | 3/1995 | Gaba | |
| 5,417,659 A | | 5/1995 | Gaba | |
| 5,601,532 A | | 2/1997 | Gaba | |
| 6,123,193 A | | 9/2000 | Vojtasek et al. | |
| 6,183,440 B1 | | 2/2001 | Bell | |
| 6,276,527 B1 | | 8/2001 | Vojtasek et al. | |
| 6,382,417 B2 | | 5/2002 | Kanner et al. | |
| 6,488,666 B1 | | 12/2002 | Geist | |

OTHER PUBLICATIONS

The Arrow Sharpsaway II, [online], Arrow International: Products {Critical Care: The Arrow Sharps Away II}, 2 pages, [retrieved on Jan. 19, 2005] retrieved from: http://www.arrowintl.com/products/critical_care/prishrt.asp.
Large Gauge Needlevise, [online] Large Guage NeedleVISE, 2 pages, [retrieved on Jul. 22, 2005], retrieved from: http://www.atrionmedical.com/Large%20 NeedleVISE.htm.
Trade Literature, Point-Lok, Devices for Specialized Needles, Providing Protection for a Variety of Needles, Portex, Inc., (2001) LT-2057 10/001 www.portexusa.com.
Trade Literature, Micro ABG, Cat No. TD053 Rev.01 Vital Signs, Inc. (2001) 2 pages.

\* cited by examiner

*Primary Examiner*—Jacob K Ackun, Jr.
*Assistant Examiner*—Robert Poon
(74) *Attorney, Agent, or Firm*—Robert G. Rosenthal

(57) ABSTRACT

Devices, systems and methods that fixably, and/or permanently capture and cover the sharp end of "sharps" in order to allow for their safe disposal. The sharps can include but are not limited to sharp medical instruments such as but not limited to syringes, needles, scalpel blades, as well as other sharp devices such as but not limited to sharp-tipped ornamental pins, sewing needles, and the like. The devices can include containers having bendable flaps which can bind against needles being inserted into the container, resilient materials, reactive chemical materials, and the like, which can also bind and/or permanently capture the sharps.

1 Claim, 30 Drawing Sheets

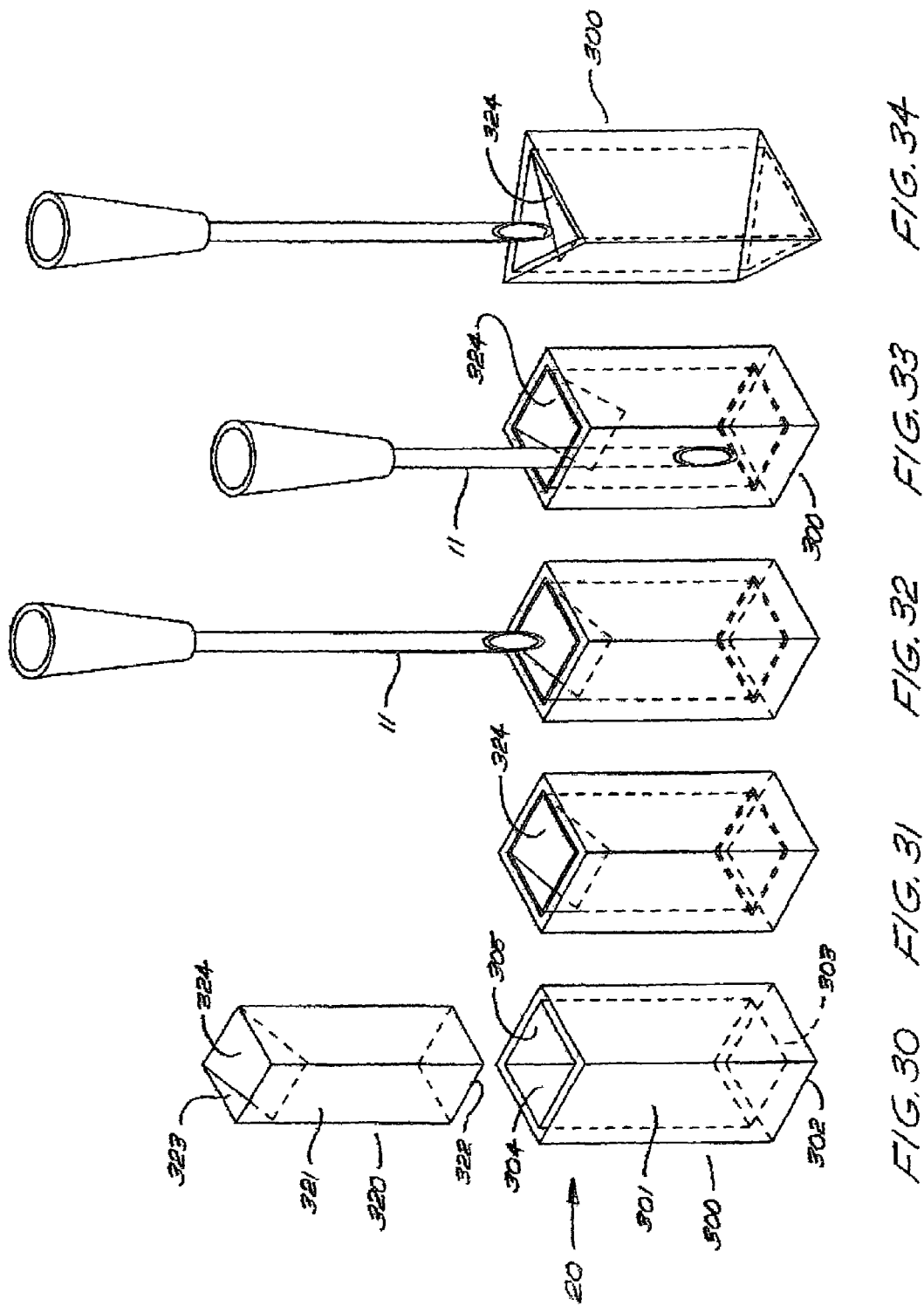

PERMANENT SHARPS CAPTURE DEVICES, SYSTEMS AND METHODS OF USE

This invention claims the benefit of priority of U.S. Provisional Patent Application Ser. No. 60/819,453 filed Jul. 7, 2006 which is a Continuation-In-Part of U.S. patent application Ser. No. 11/399,201 filed Apr. 6, 2006, which claims the benefit of priority to U.S. Provisional Patent Application Ser. No. 60/669,539 filed Apr. 8, 2005.

FIELD OF THE INVENTION

This invention relates, generally, to devices that are used to prevent injuries related to the use and disposal of sharp medical instruments, commonly known as "sharps" and more specifically to protecting human beings from unintentional needle-sticks when handling used "sharps" such as but not limited to syringes, needles, scalpel blades, sharp-tipped ornamental pins, sewing needles, and the like, and, more specifically, to devices, systems and methods that permanently capture and cover the sharp end of a "sharps" in order to allow for safe disposal of such "sharps."

BACKGROUND AND PRIOR ART

Injuries from handling sharp medical instruments, such as but not limited to syringes, needles, scalpel blades, and other sharp devices, such as but not limited to sharp-tipped ornamental pins, sewing needles, and the like, all commonly referred to as "sharps" to rise in the world and especially in the healthcare profession. In addition, the distress, sickness and absenteeism resulting from sharps injuries constitute a considerable strain on the already limited human resources in the medical profession.

Several attempts have been made to address the problems and dangers associated with the proper disposal of used and possibly contaminated "sharps" such as syringe needles. Generally, the attempts have involved complex shielding devices configured to attach to a conventional syringe or, so called, "safety-Syringes" that have various forms of "automatic" safety shields.

Other attempts has disposal have included devices designed to burn or melt a used needles or to capture a needle within a complex roller-binding mechanism. Most of these devices are costly or complex. It should be noted, that the cost of a "single-use" syringe is very low and that adding a complex and expensive device is prohibitive. There are also medical practices that involve the use of re-usable syringes with disposable needles. In these instances, there remains a need for a safe, efficient and cost effective way to dispose of, or re-cap a used and possibly contaminated syringe or I/V (intravenous) needle.

The subject of inventor's pending U.S. patent application Ser. No. 11/399,201 filed Apr. 6, 2006, which claims the benefit of priority to U.S. Provisional Patent Application Ser. No. 60/669,539 filed Apr. 8, 2005, both of which are incorporated by reference, addresses the recapping issues by providing a shield that can completely cover and encapsulates the pointed end of a syringe needle. A plurality of shields is placed in a holding tray so that a used syringe or I/V needle may be inserted into a shield. The shields comprise of rigid, preferably metal, shell having a closed distal end and an open proximal end and an elastomeric capturing material within the shell. The shielded needle may be safely recapped while the capture shield is in place. In addition the material disclosed prevents the needle from leaking into an area where there may be exposure to a human being. The capture modules are configured to be mechanically attached to an inserted needle by the properties of an elastomeric material into which the needle is inserted. It is obvious that, while the attachment is sufficient for safe recapping of the needle, it is not sufficient for disposal without the step of recapping since the capture module may be physically removed with sufficient force applied to remove it.

Thus, the need exists for a needle shield that cannot be removed so that a needle is permanently captures or shielded whether or not it is to be recapped for disposal.

SUMMARY OF THE INVENTION

A primary objective of the present invention is to provide devices, systems and methods that permanently capture and cover the sharp end of a "sharps" such as but not limited to medical syringes, needles, scalpel blades, sharp-tipped ornamental pins, sewing needles, and the like.

A secondary objective of the present invention is to provide devices, systems and methods that allow for the safe disposal of "sharps" such as but not limited to medical syringes, needles, scalpel blades, sharp-tipped ornamental pins, sewing needles, and the like.

A preferred embodiment, includes a containment member into which a used needle can be irreversibly inserted. The preferred embodiment additionally contemplates that a plurality of containment members is arranged in a matrix so that the containment members are easily penetrable by a used needle.

A captured or shielded syringe needle can be removed from a holding tray and safely transported for recapping or disposal.

One preferred embodiment of needle capture device can include an elongate metal channel having, at least, a hinged end flap sized and configured to allow a needle to pass into said channel in a first direction, where said end flap binds upon said needle when a force is applied to move said needle in a second direction.

Another preferred embodiment of needle capture device can include an elongate metal channel having a first hinged end flap extending from a first channel wall, where said first end flap is sized and configured to allow a needle to pass into said channel in a first direction, and where said end flap binds upon said needle when a force is applied to move said needle in a second direction; and a second hinged end flap extending from a second, opposing channel wall, where said second end flap is sized and configured to allow a needle to pass into said channel in a second direction, and where said end flap binds upon said needle when a force is applied to move said needle in a first direction, and where the hinged portions of the end flaps are arranged so that a needle extending through a first end flap is forced into the acute angular internal hinge portion of the second end flap, and where the hinged portions of the end flaps are arranged so that a needle extending through a second end flap is forced into the acute angular internal hinge portion of the first end flap.

Another preferred embodiment of needle capture device can include a capture element sized and configured to seize a needle in a binding arrangement; and a holding member sized and configured to hold a plurality of capture elements so that said capture elements can be accessed by a user.

Another preferred embodiment of needle capture device can include a permanent capture element sized and configured to irreversibly seize a needle in a binding arrangement; and a holding member sized and configured to hold a plurality of capture elements so that said capture elements can be accessed by a user.

Another preferred embodiment of needle capture device can include a permanent capture element sized and configured to irreversibly seize a needle in a binding arrangement; and a holding member sized and configured to hold a plurality of capture elements so that said capture elements can be accessed by a user.

Another preferred embodiment of needle capture device can include a permanent capture element sized and configured to irreversibly seize a needle in a bonded arrangement; and a holding member sized and configured to hold a plurality of capture elements so that said capture elements can be accessed by a user.

Another preferred embodiment of needle capture device can include a permanent capture element sized and configured to irreversibly seize a needle in a bonded arrangement where said bonded arrangement comprises a reactive chemical in a sealed container that can be breached by a sharp needle so that said reactive chemical can be dispersed as said needle passes through said reactive chemical; and a holding member sized and configured to hold a plurality of capture elements so that said capture elements can be accessed by a user.

Another preferred embodiment of needle capture device can include a permanent capture element sized and configured to irreversibly seize a needle in a bonded arrangement where said bonded arrangement comprises two-part reactive chemicals in a sealed container that can be breached by a sharp needle so that said two-part reactive chemicals can be mixed or dispersed as said needle passes through said reactive chemicals; and a holding member sized and configured to hold a plurality of capture elements so that said capture elements can be accessed by a user.

Another preferred embodiment of needle capture device can include a permanent capture element sized and configured to irreversibly seize a needle in a bonded arrangement where said bonded arrangement comprises a reactive adhesive chemical in a sealed container that can be breached by a sharp needle so that said reactive adhesive chemical can be dispersed into a preferred medium such as cotton as said needle passes through said reactive chemical; and a holding member sized and configured to hold a plurality of capture elements so that said capture elements can be accessed by a user.

Another preferred embodiment of needle capture device can include a permanent capture element sized and configured to irreversibly seize a needle in a bonded arrangement where said bonded arrangement comprises a reactive adhesive chemical such as cyanoacrylate in a sealed container that can be breached by a sharp needle so that said reactive adhesive chemical can be dispersed into a preferred medium such as cotton as said needle passes through said reactive chemical; and a holding member sized and configured to hold a plurality of capture elements so that said capture elements can be accessed by a user.

A novel method of capturing a needle, can include the steps of inserting a sharp end of a needle into a container; and binding the needle inside of the container, wherein the needle is captured for disposal.

The step of binding can include the steps of bending a flap inside the container by the sharp end of the needle; and trapping the sharp end of the needle inside of the container, by the flap.

The step of binding can include the steps of bending a second bendable flap inside the container by the sharp end of the needle; and trapping the sharp end of the needle inside of the container, by the first and second flap.

The step of binding can include the steps of a permanent capture element sized and configured to irreversibly seize a needle.

The permanent capture element can include a resilient material. The permanent capture element can also include a foam material.

The permanent capture element can include a bonded arrangement where said bonded arrangement comprises a reactive chemical in a sealed container that can be breached by a sharp needle so said reactive chemical can be dispersed as said needle passes through said reactive chemical.

The permanent capture element can include a bonded arrangement that comprises two-part reactive chemicals in a sealed container that can be breached by a sharp needle so said two-part reactive chemicals can be mixed or dispersed as said needle passes through said reactive chemicals.

The permanent capture element can include a bonded arrangement that comprises a reactive adhesive chemical in a sealed container that can be breached by a sharp needle so said reactive adhesive chemical can be dispersed into a preferred medium such as cotton as said needle passes through said reactive chemical.

The permanent capture element can include a bonded arrangement that comprises a reactive adhesive chemical such as cyanoacrylate in a sealed container that can be breached by a sharp needle so that said reactive adhesive chemical can be dispersed into a preferred medium such as cotton as said needle passes through said reactive chemical.

Further objects and advantages of this invention will be apparent from the following detailed description of the presently preferred embodiments which are illustrated schematically in the accompanying drawings.

BRIEF DESCRIPTION OF THE FIGURES

FIG. 30 is an exploded view of an alternate embodiment of a binding capture element with a plastic shell.

FIG. 31 illustrates an assembled alternate embodiment of a binding capture element with a plastic shell.

FIG. 32 illustrates an assembled alternate embodiment of a binding capture element with a plastic shell with a needle approaching the open end.

FIG. 33 illustrates an assembled alternate embodiment of a binding capture element with a plastic shell with a needle within the channel.

FIG. 34 illustrates further alternate embodiment illustrating an alternate profile.

DESCRIPTION OF THE PREFERRED EMBODIMENTS

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

Figure 1:
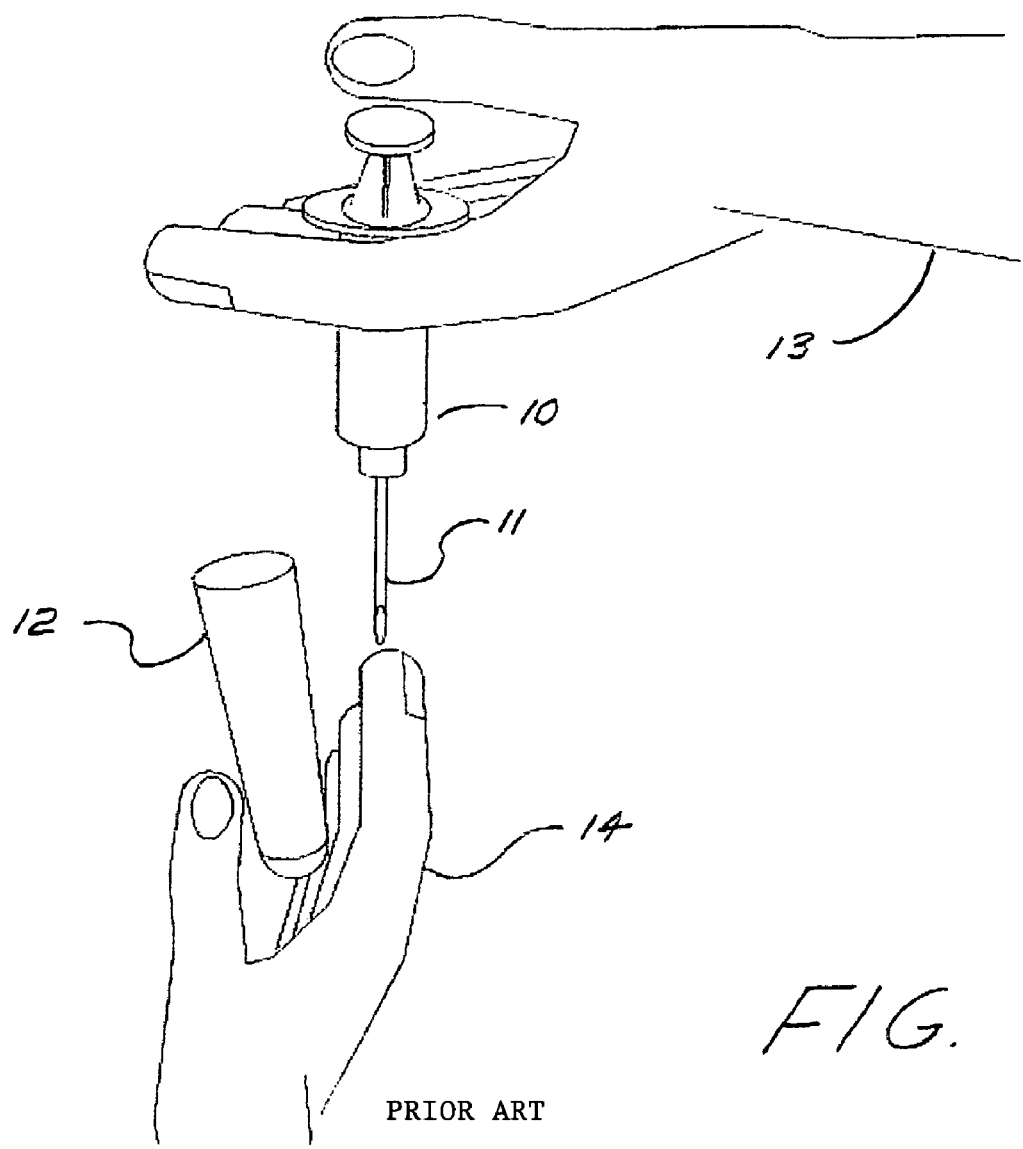
FIG. 1 illustrates the risk associated with recapping a used syringe with an attached needle.
Figure 2:
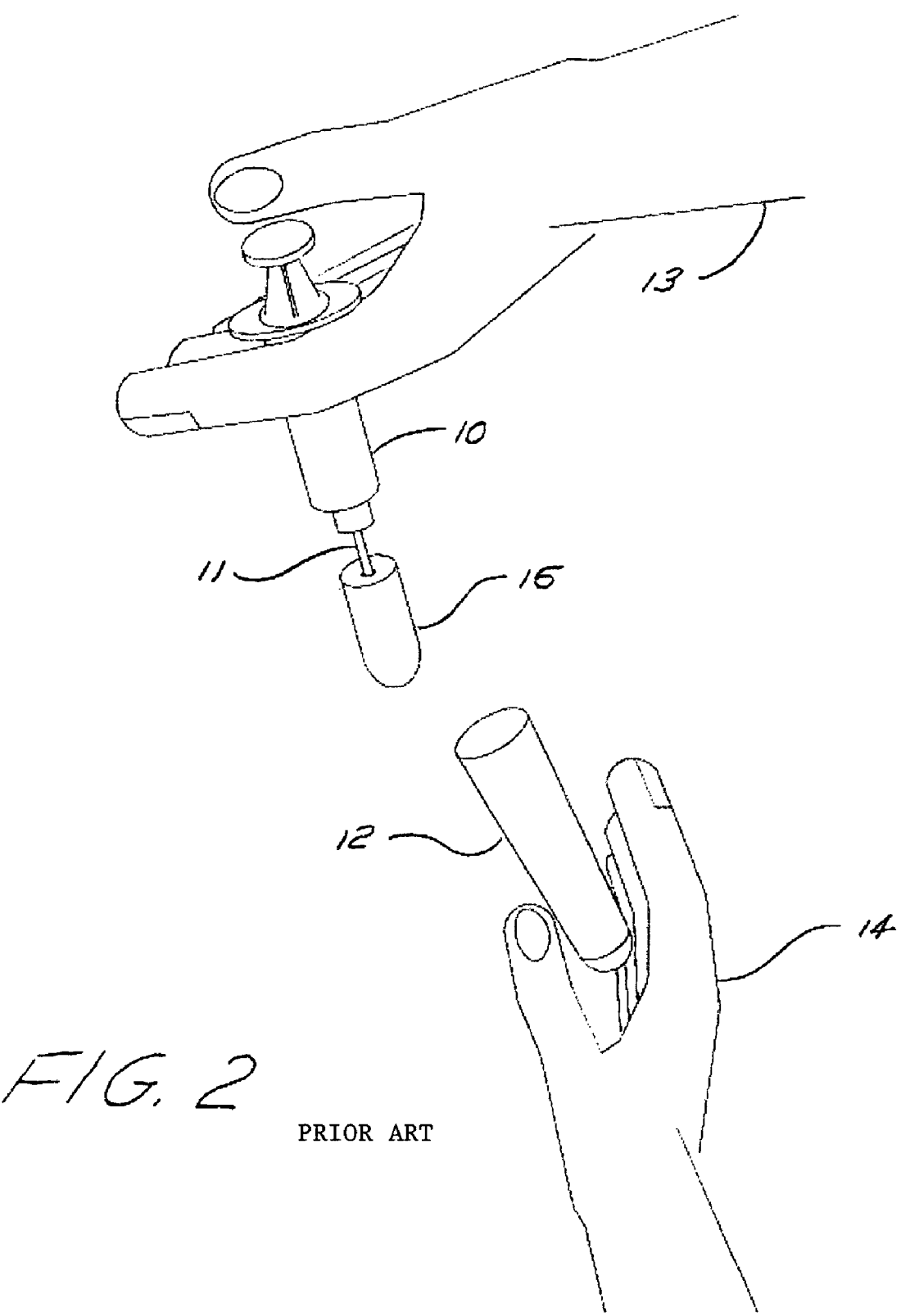
FIG. 2 illustrates a shielding member according to prior art as described in the inventor's pending U.S. patent application Ser. No. 11/399,201 filed Apr. 6, 2006, associated with a syringe and needle.
Figure 3:
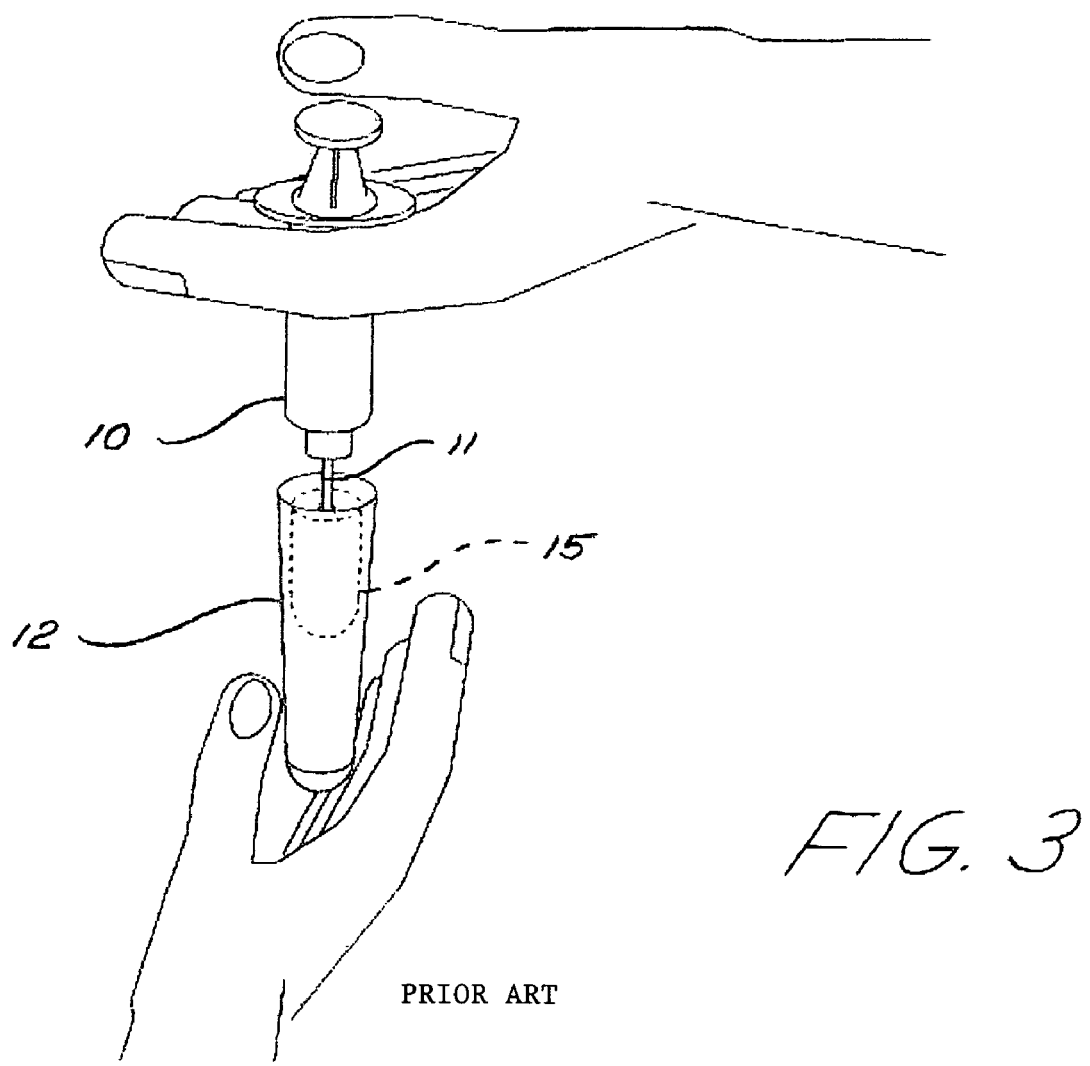
FIG. 3 illustrates a shielding member according to prior art inventor's pending U.S. Patent Application 11/399,201 filed Apr. 6, 2006, associated with a syringe and needle and a needle cap.

FIGS. 1-3 illustrates the inventor's pending U.S. patent application Ser. No. 11/399,201 filed Apr. 6, 2006, which claims the benefit of priority to U.S. Provisional Patent Application Ser. No. 60/669,539 filed Apr. 8, 2005, both of which are incorporated by reference. A used and possibly contaminated syringe 10 needle 11 can be recapped in a two-handed 13, 14 operation. The recapping procedure presents the risk of unintentional needle stick injury.

As one hand 13 holds the syringe 10, the needle 11 point is advanced toward the cap 12 which is held in the other hand 14 of the operator. Unless a user is very familiar with the recapping procedure, has adequate hand-eye coordination and gives the procedure full attention it is quite possible to stick the pointed end of a contaminated needle into the hand holding the needle cap. In order to minimize the risk of needle stick injuries, a temporary capture-shield 15 is disclosed into which a used needle 11 is inserted.

The capture-shield 15 can be sized and configured to adhere to the needle 11 by elastic compression of the material within the capture-shield 15. Various elastic materials are disclosed that hold a needle 11 adequately for safe recapping 12. A plurality of shields 15 can be provided in a holding supply-tray so that a used syringe needle 11 can be captured within one of the shields 15 and subsequently the shield 15 and captured needle 11 can be removed from the holding tray so that the needle 11 may be safely transported or recapped. The shields 15 are sized and configured to fit within a needle cap 12 associated with the needle 11. If the operator fails to align the captured needle 11 with the lumen of the needle cap 12, no injury to the operator will occur.

Figure 4:
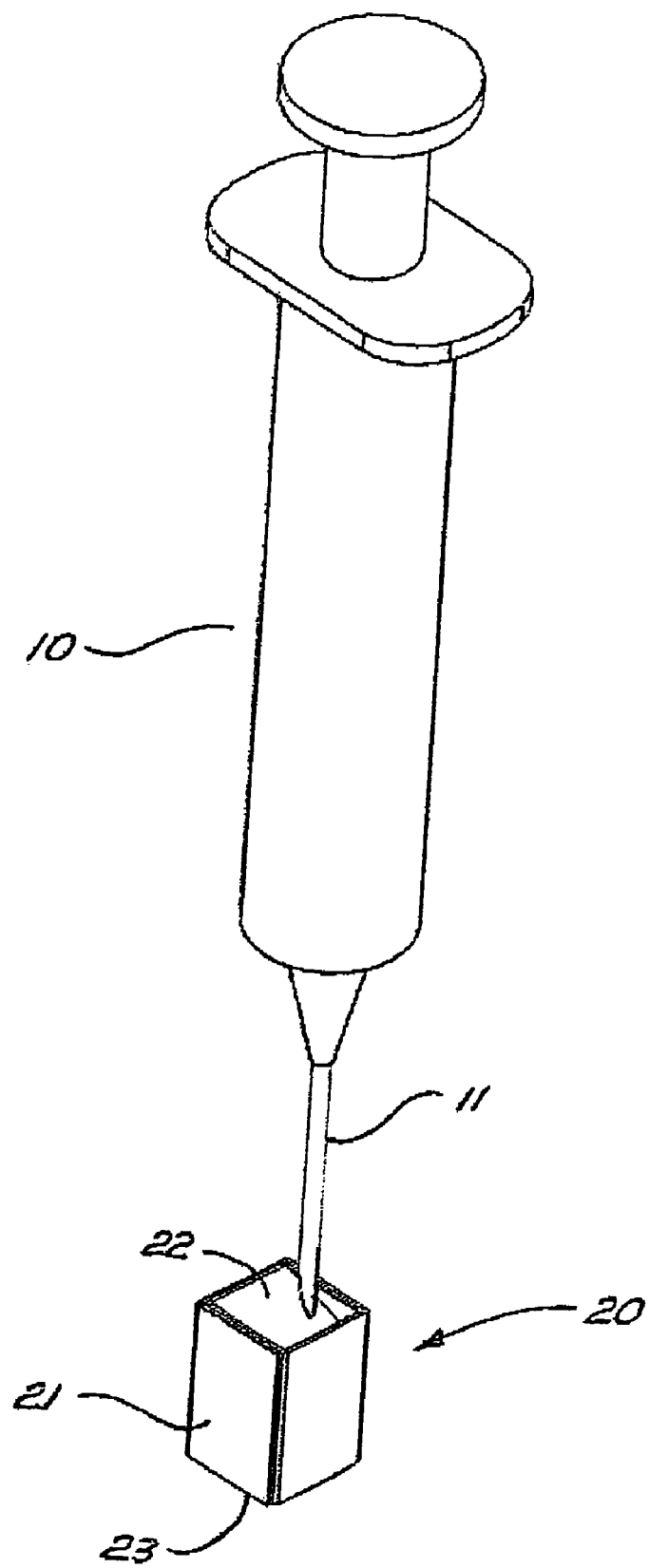
FIG. 4 is a perspective view of a syringe, needle and a permanent, mechanical capture member according to the present invention.
Figure 5:
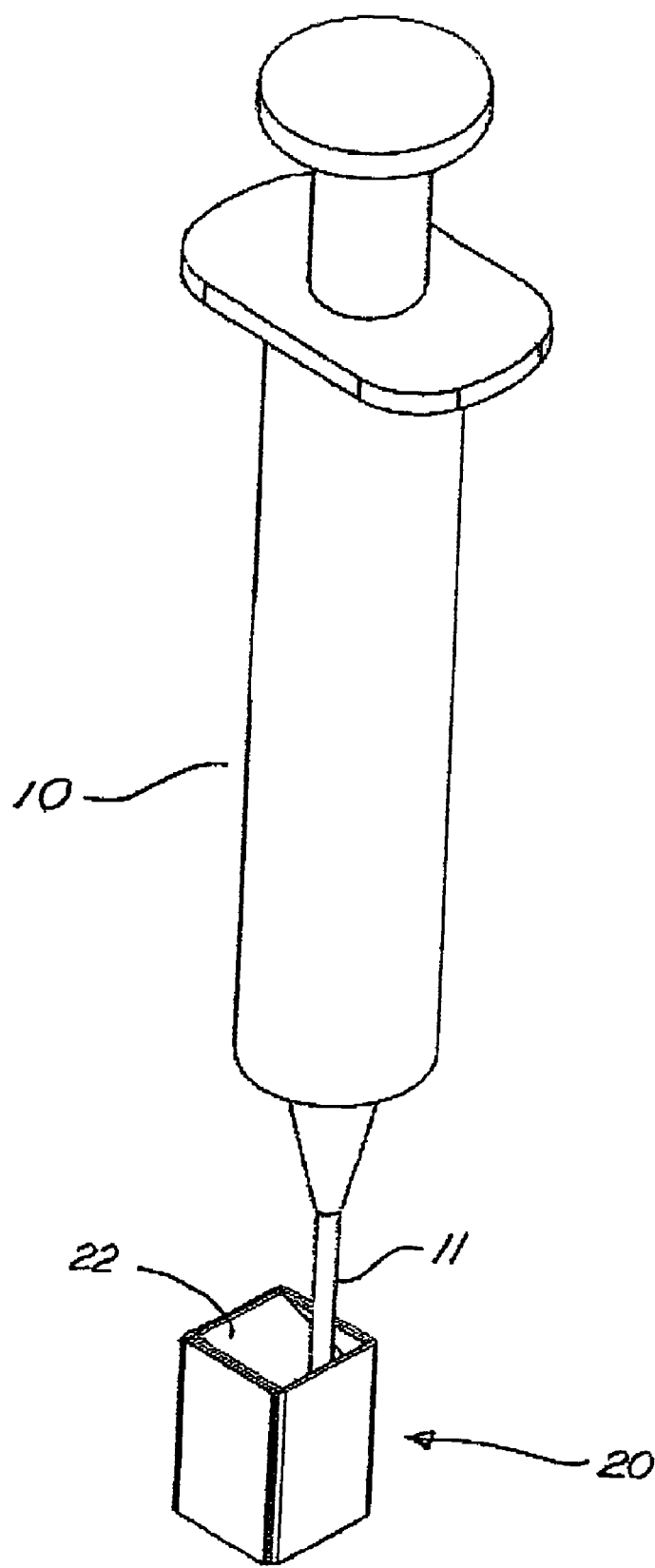
FIG. 5 illustrates a syringe needle captured by the present invention.
Figure 6:
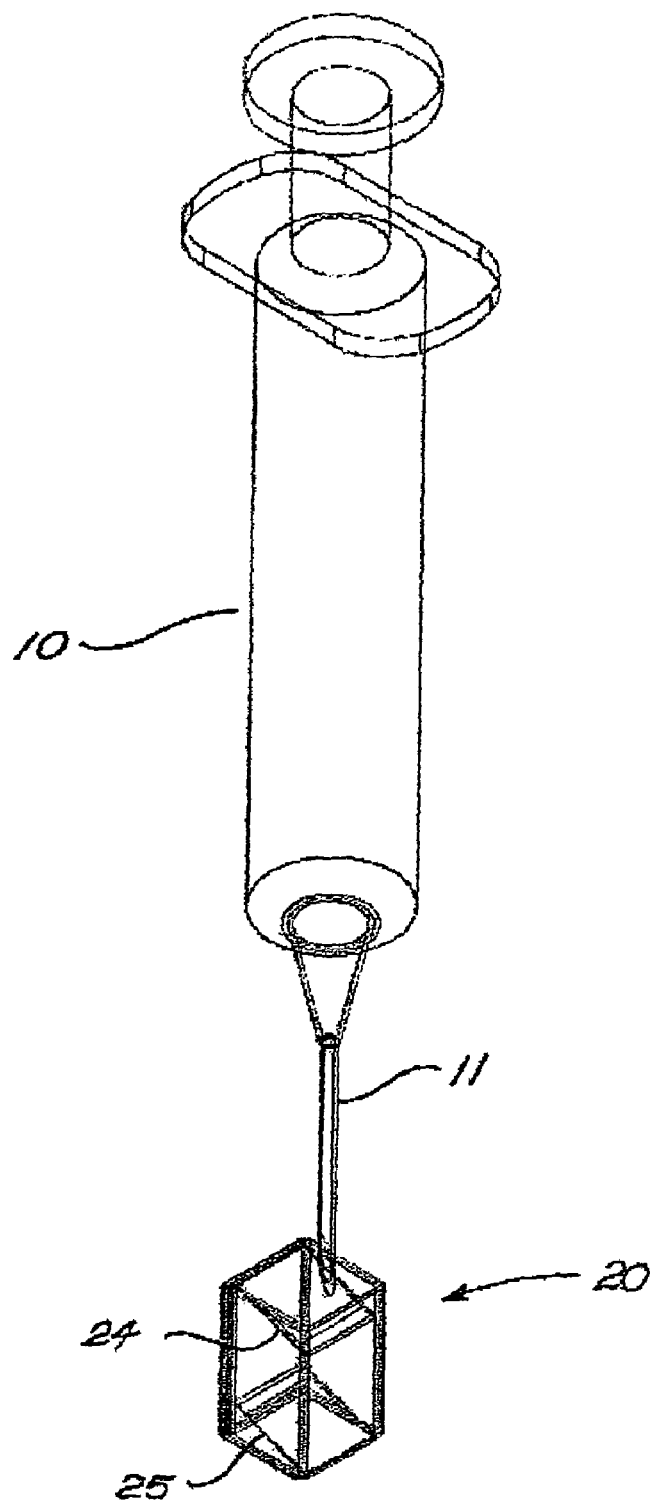
FIG. 6 is a perspective section view of a syringe, needle and capture member according to the present invention.
Figure 7:
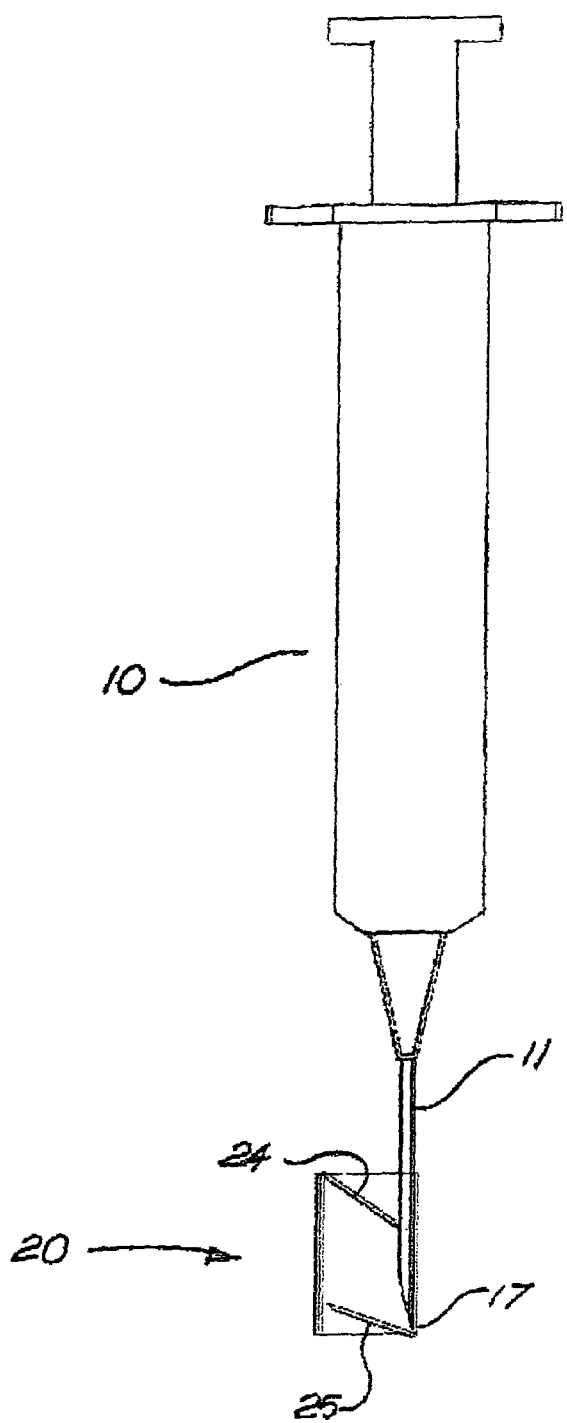
FIG. 7 is a side section view of a syringe needle captured by the present invention.
Figure 8:
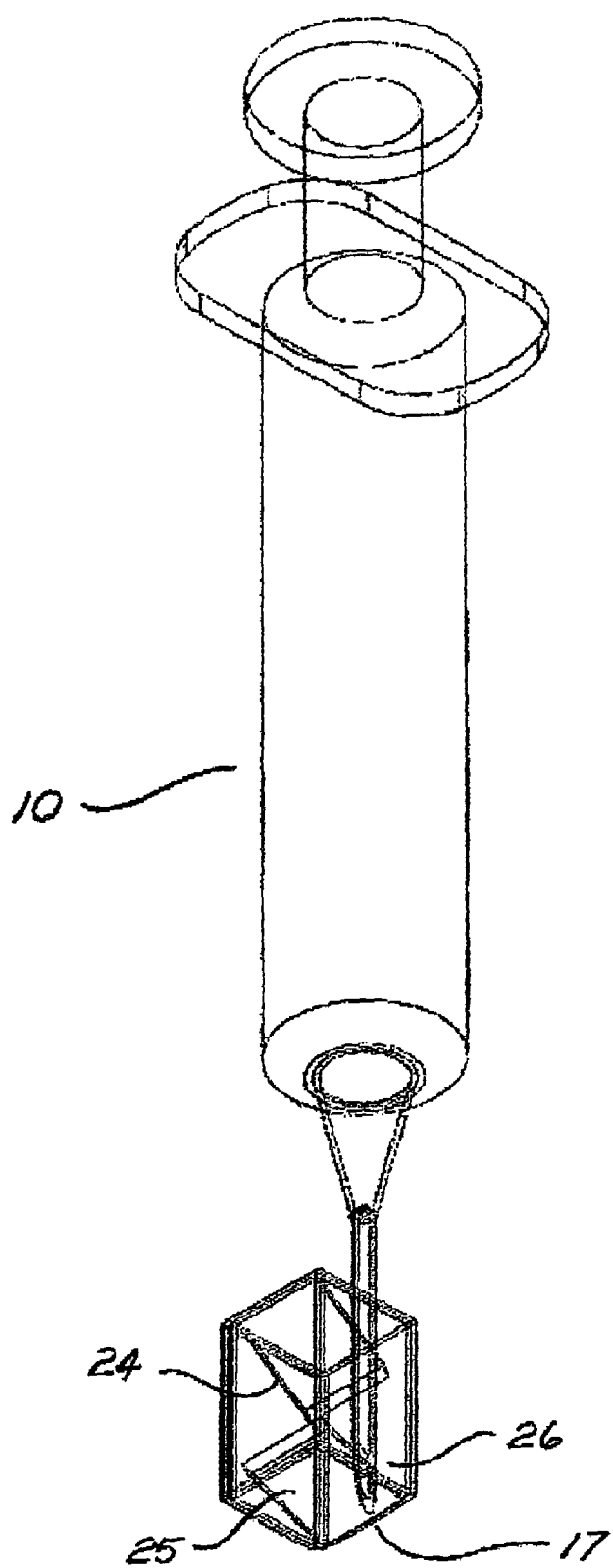
FIG. 8 is a perspective section view of a syringe needle captured by the present invention.
Figure 9:
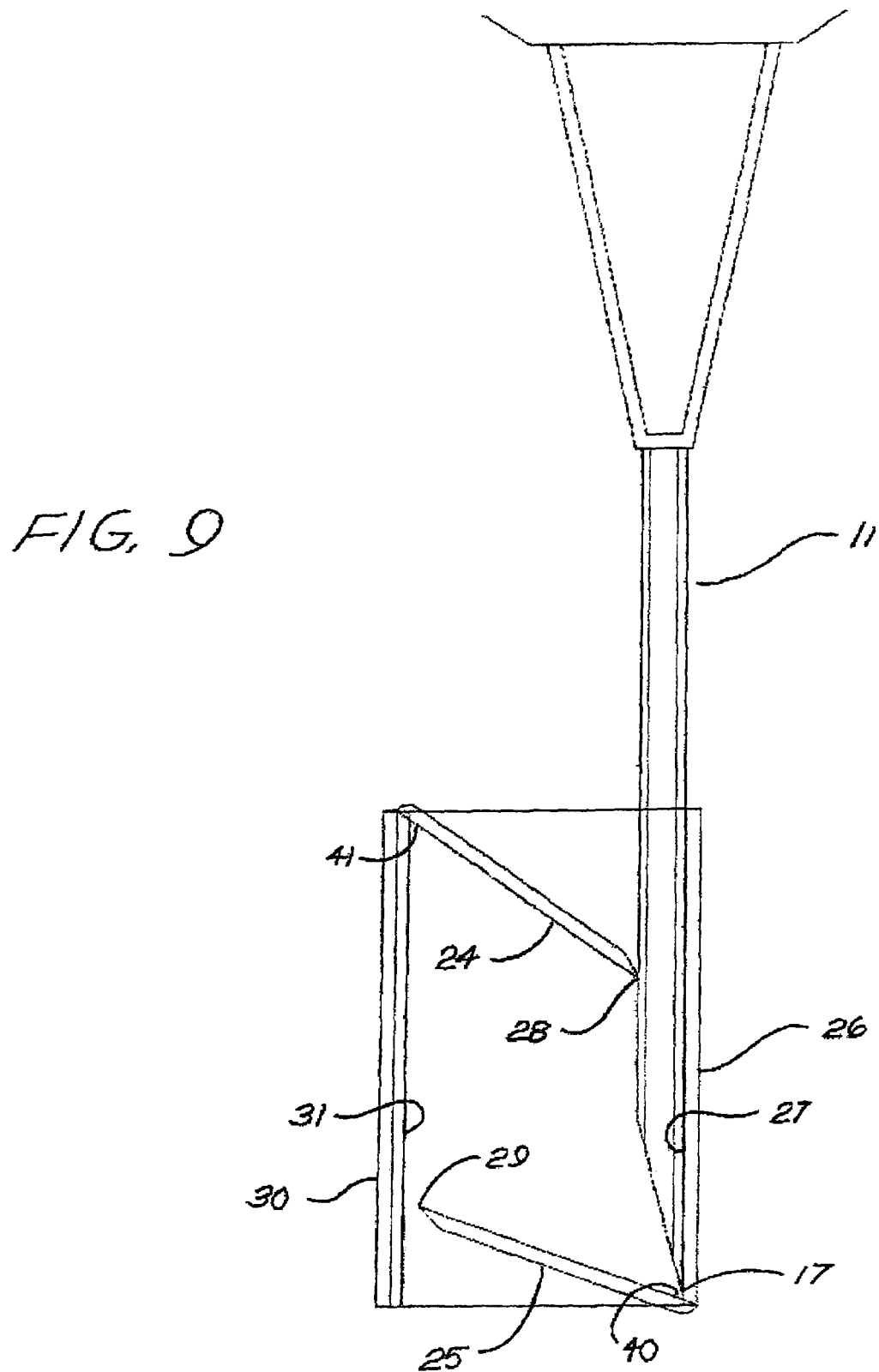
FIG. 9 is an enlarged detailed view of the present invention with a captured needle.

FIG. 4 is a perspective view of a syringe, needle and a permanent, mechanical capture member according to the present invention. FIG. 5 illustrates a syringe needle captured by the present invention. FIG. 6 is a perspective section view of a syringe, needle and capture member according to the present invention. FIG. 7 is a side section view of a syringe needle captured by the present invention. FIG. 8 is a perspective section view of a syringe needle captured by the present invention. FIG. 9 is an enlarged detailed view of the present invention with a captured needle.

Referring now to FIGS. 4-9 a permanent needle capture element 20 is shown comprising a generally elongate rectangular, box shaped channel 21 having four side walls, a first penetrable end 22 and a second penetrable end 23. In a first preferred embodiment the capture element 20 can be constructed of thin sheet metal that is folded into an elongate channel 21. A first end 22 of the channel 21 comprises a flap 24 that extends from a first wall 31 downward toward the opposite wall 27 across the lumen of the channel 21 at an angle toward the second end 23 of the channel 21. The second end 23 of the channel 21 comprises a second flap 25 that extends from a second wall 27 toward the opposite wall 31 across the lumen of the channel 21 at an angle up toward the first end 22 of the channel 21.

A sharp ended object, such as but not limited to a syringe, I/V needle, biopsy needle, insufflation needle or the like, 11, can be inserted into the lumen of the channel 21 from either end 22, 23 and then displaces an end flap 24, 25 inwardly toward the opposite end of the channel. A binding force can be created when an attempt is made to withdraw a needle 11 from within the channel 21. There can be insufficient room between the extended end 28 of the end flaps and the opposing wall surfaces 27, 31 to allow the needle 11 to escape from the channel 21.

A fully inserted needle 11 can extend to the opposite end of the channel 21 and come to rest at the folded hinge-point 40, 41 of the opposite end flap 24, 25. In addition, the binding force can be concentrated by sharpening the extending ends 28, 29 of the end flaps 24, 25. Additional traction can also be supplied by providing the opposing wall surfaces 27, 31 with a texture or grit.

Figure 10:
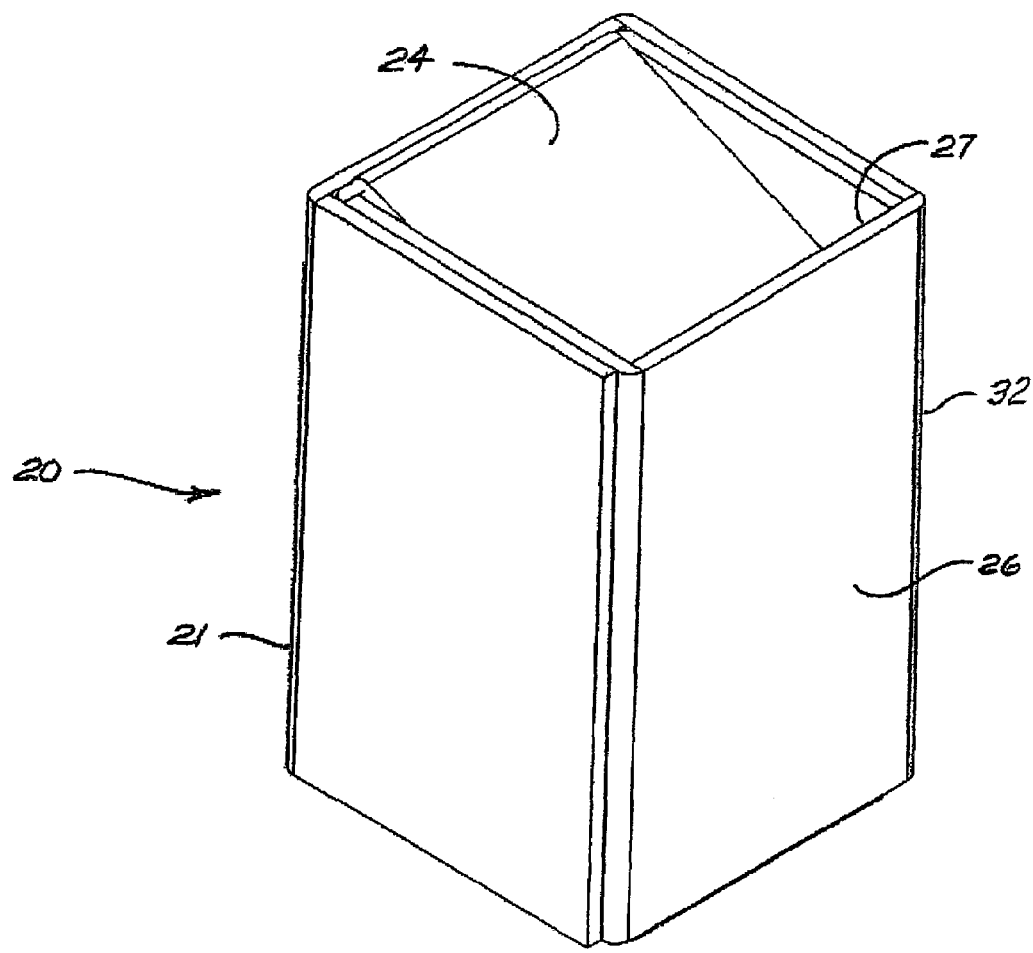
FIG. 10 is a side perspective illustration of a preferred embodiment of the capture member.
Figure 11:
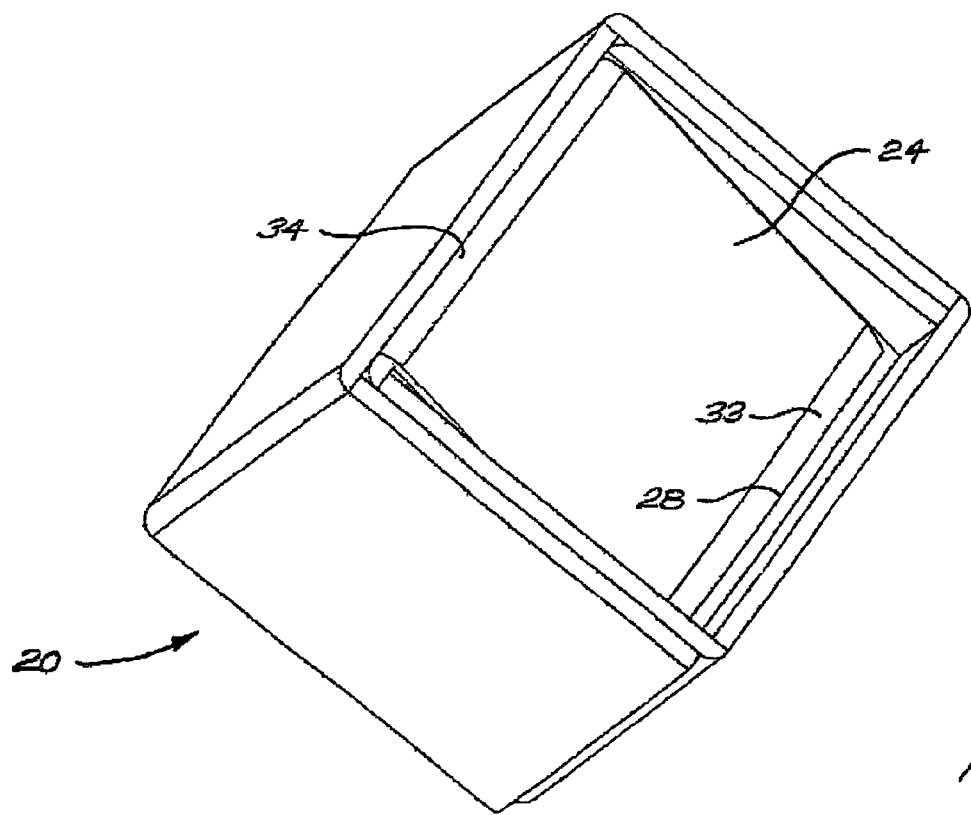
FIG. 11 is a top perspective illustration of a preferred embodiment of the capture member.
Figure 12:
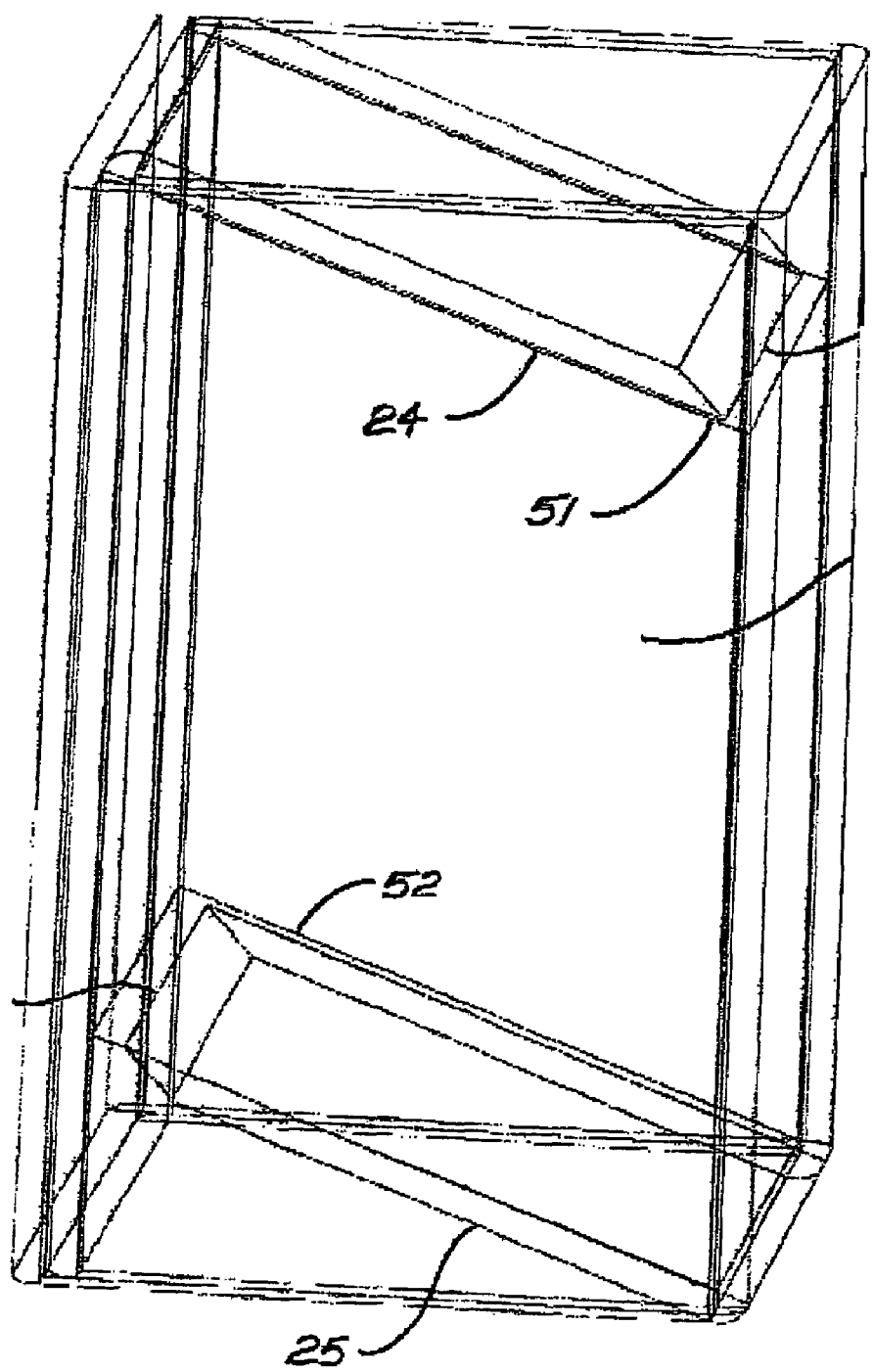
FIG. 12 is a side perspective section view of a preferred embodiment of the capture member.
Figure 13:
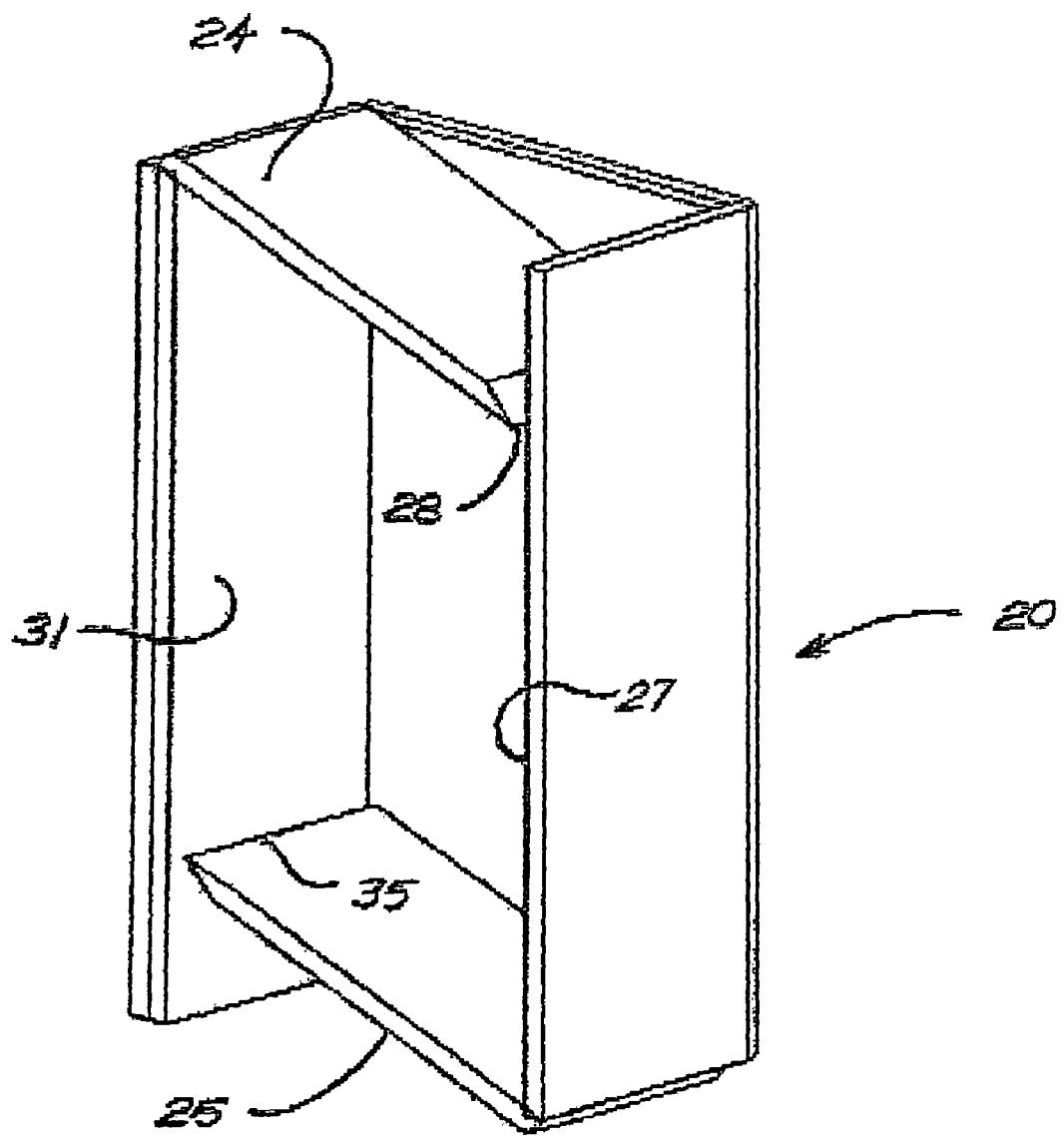
FIG. 13 is a side, cut-away perspective view of a preferred embodiment of a capture member.
Figure 14:
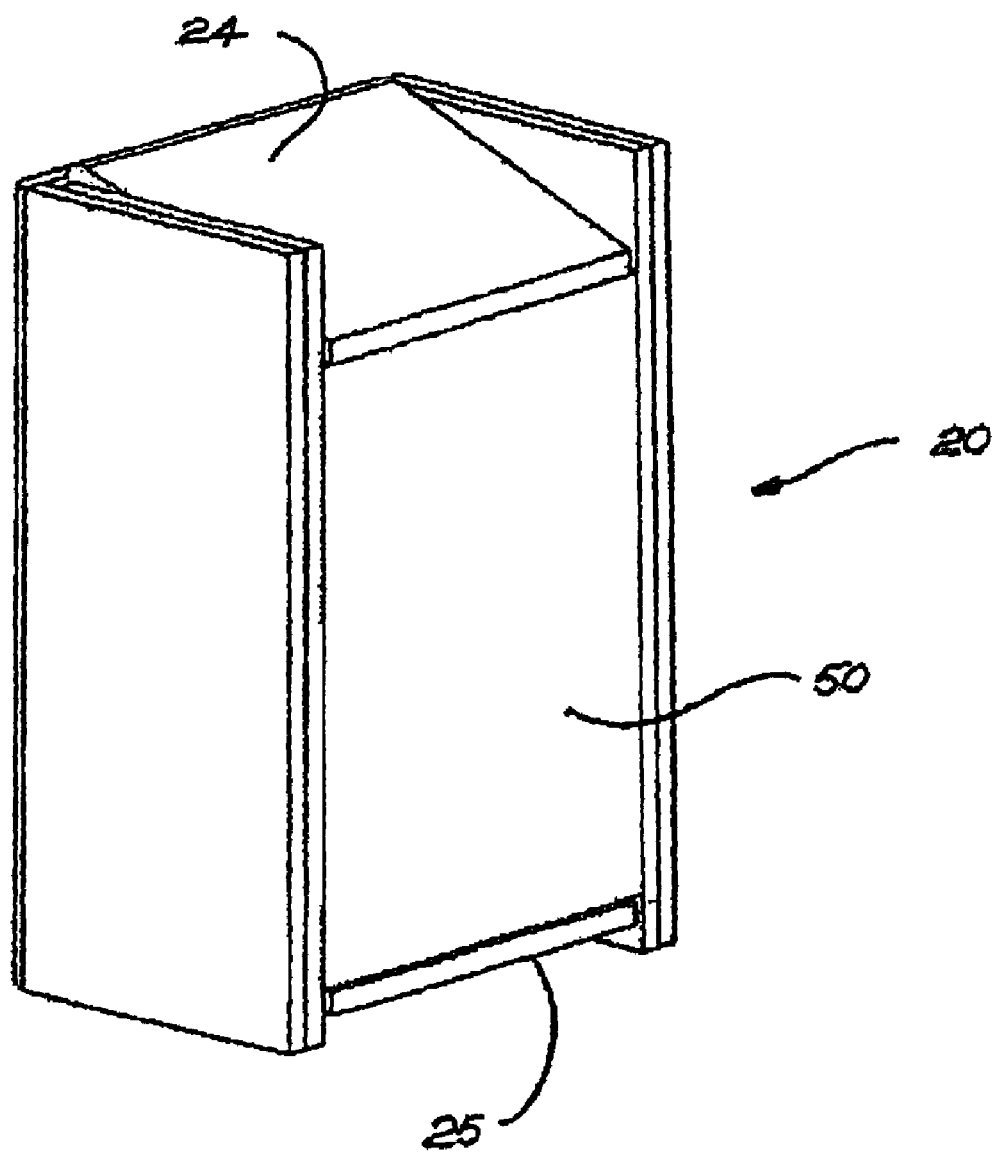
FIG. 14 is a front, cut-away perspective view of a preferred embodiment of a capture member.

FIG. 10 is a side perspective illustration of a preferred embodiment of the capture member. FIG. 11 is a top perspective illustration of a preferred embodiment of the capture member. FIG. 12 is a side perspective section view of a preferred embodiment of the capture member. FIG. 13 is a side, cut-away perspective view of a preferred embodiment of a capture member. FIG. 14 is a front, cut-away perspective view of a preferred embodiment of a capture member.

FIGS. 10-14 further illustrate the construction of a preferred embodiment of the capture element 20 where the walls 26 of the elongate channel 20 are formed by folding the wall material so that the walls 26 are double layered. The strength of the walls 26 can be increased by the double layer of material while the end flaps 24, 25 remain relatively flexible.

A shaped filler 50 such as but not limited to resilient foam, gel, and the like, can be inserted between the opposing end flaps 24, 25. The resilient material 50 adds a binding bias to the end flaps 24, 25 so that a needle 11 can be firmly held within the capture element 20.

An additional embodiment of the shaped filler 50 can comprises an element constructed from a thermoplastic material such as but not limited to polyolefin hot melt adhesive that can be extremely tacky. The adhesive material cooperates with the end flaps 24, 25 to secure a captured needle 11 within the channel 21 of capture element 20.

In a preferred embodiment, the capture element channel 21 can be folded so that the walls 26 are complete and a single "spot-weld" is provided to secure the channel 21. The first end flap 24 can then formed inwardly toward the opposite end. Next, the resilient material 50 is inserted and the second end flap 25 is formed inwardly toward the opposite end. An alternate embodiment can eliminate the double end flap and provide a substantially closed second end.

A preferred embodiment comprises a double ended flap construction so that when the captures 20 are assembled into a holding member or tray 100, they can be placed most efficiently without the chance of an upside-down placement. Additionally, the inward bias of the opposing flap 24, 25 maintains the needle point 17 in a preferred condition and position away from any open regions associated with the construction.

Figure 15:
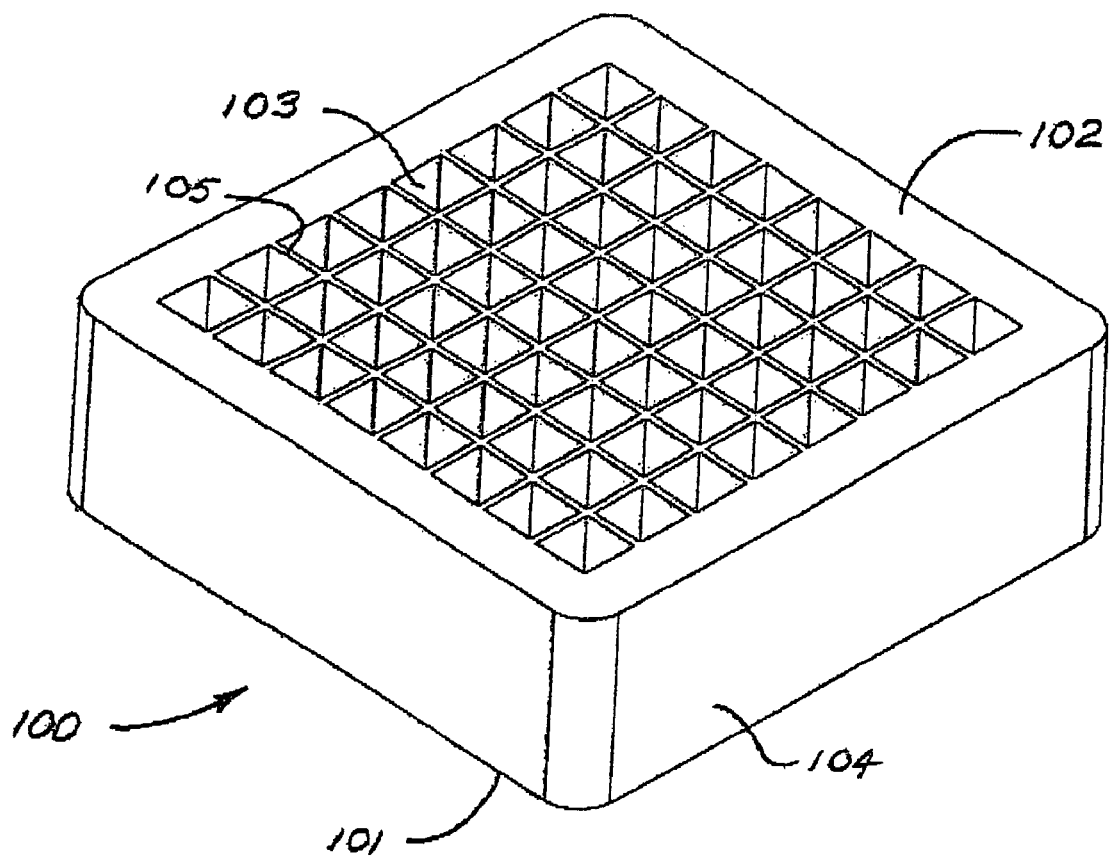
FIG. 15 illustrates a preferred holder for a plurality of capture members according to the present invention.
Figure 16:
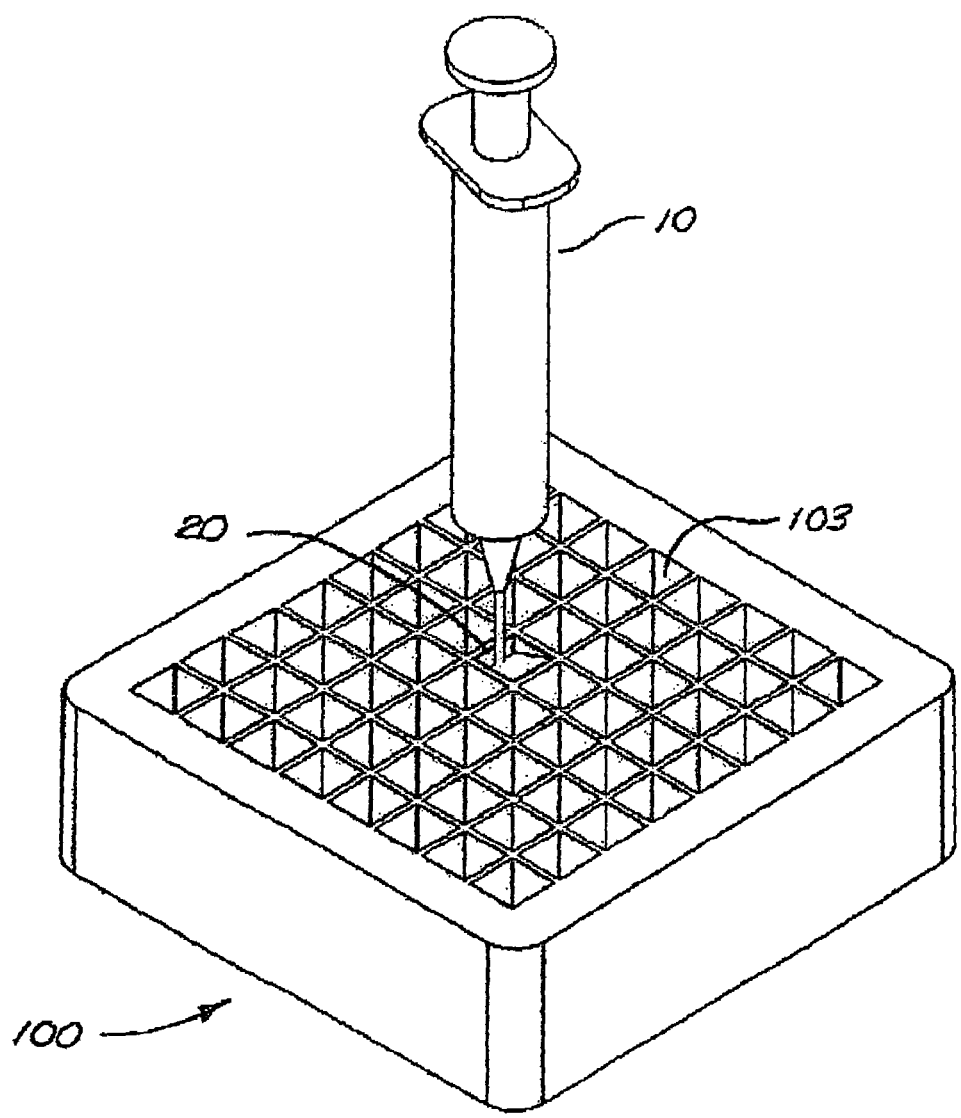
FIG. 16 is a top perspective view of a syringe needle being placed into a capture member within a holding member.
Figure 17:
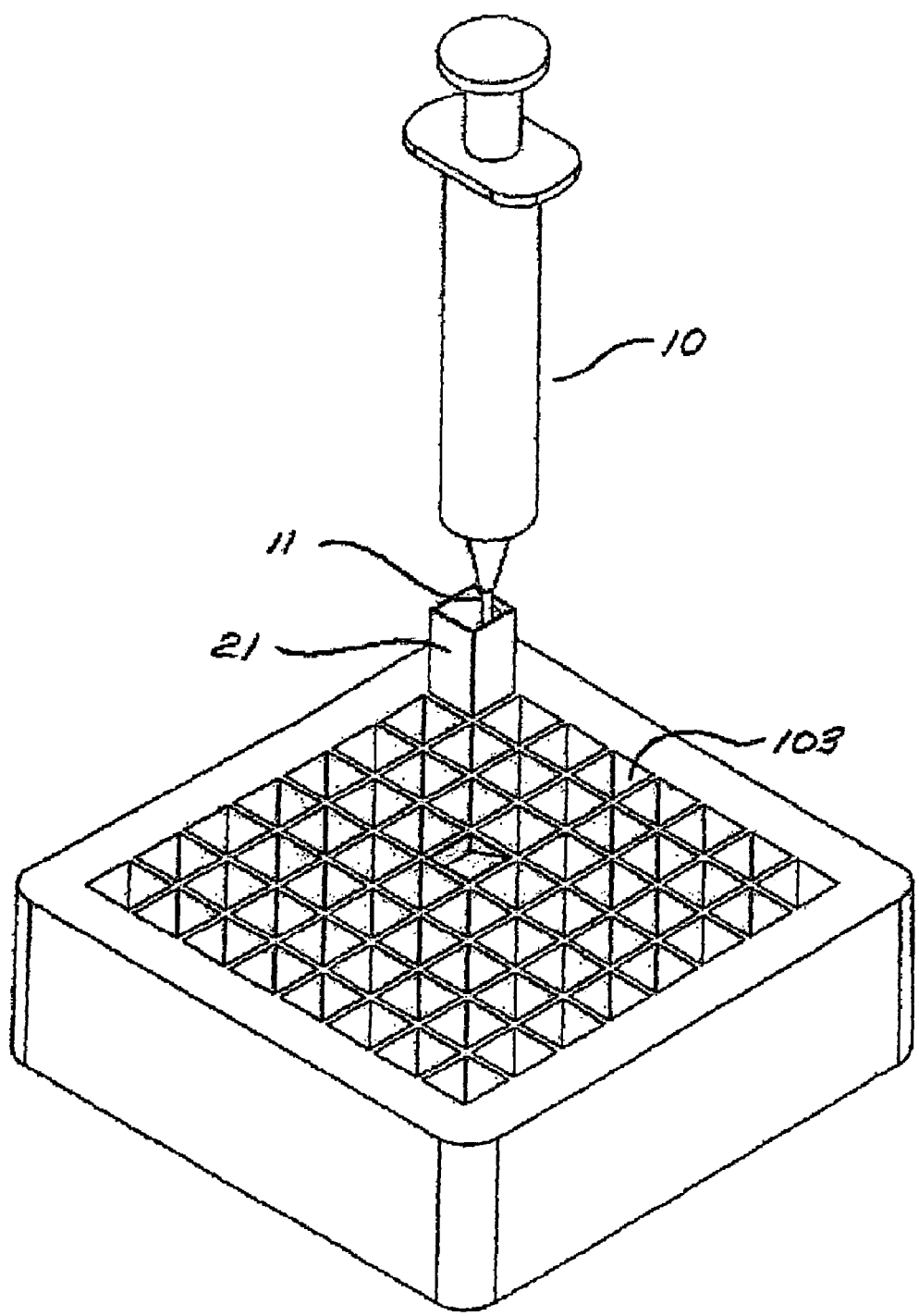
FIG. 17 is a top perspective view of a syringe needle being withdrawn with a capture member from within a holding member.
Figure 18:
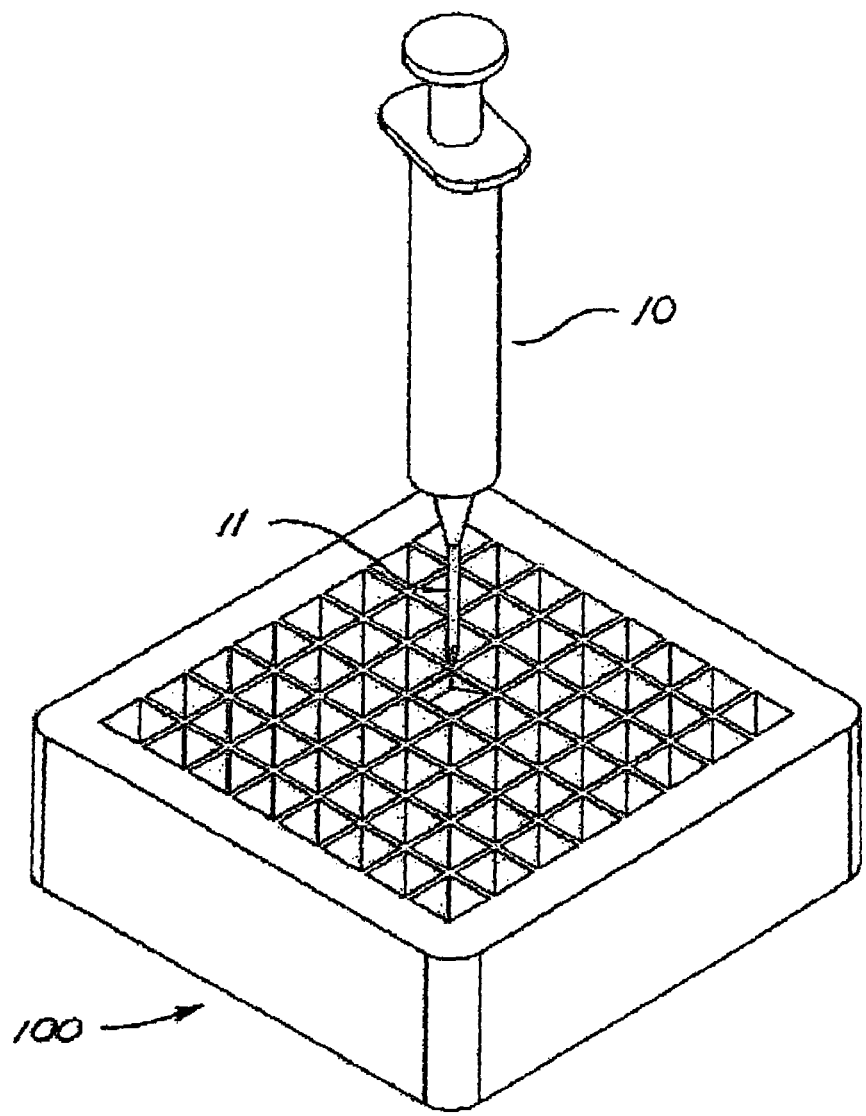
FIG. 18 is a perspective view of the arrangement of components according to the present invention.
Figure 19:
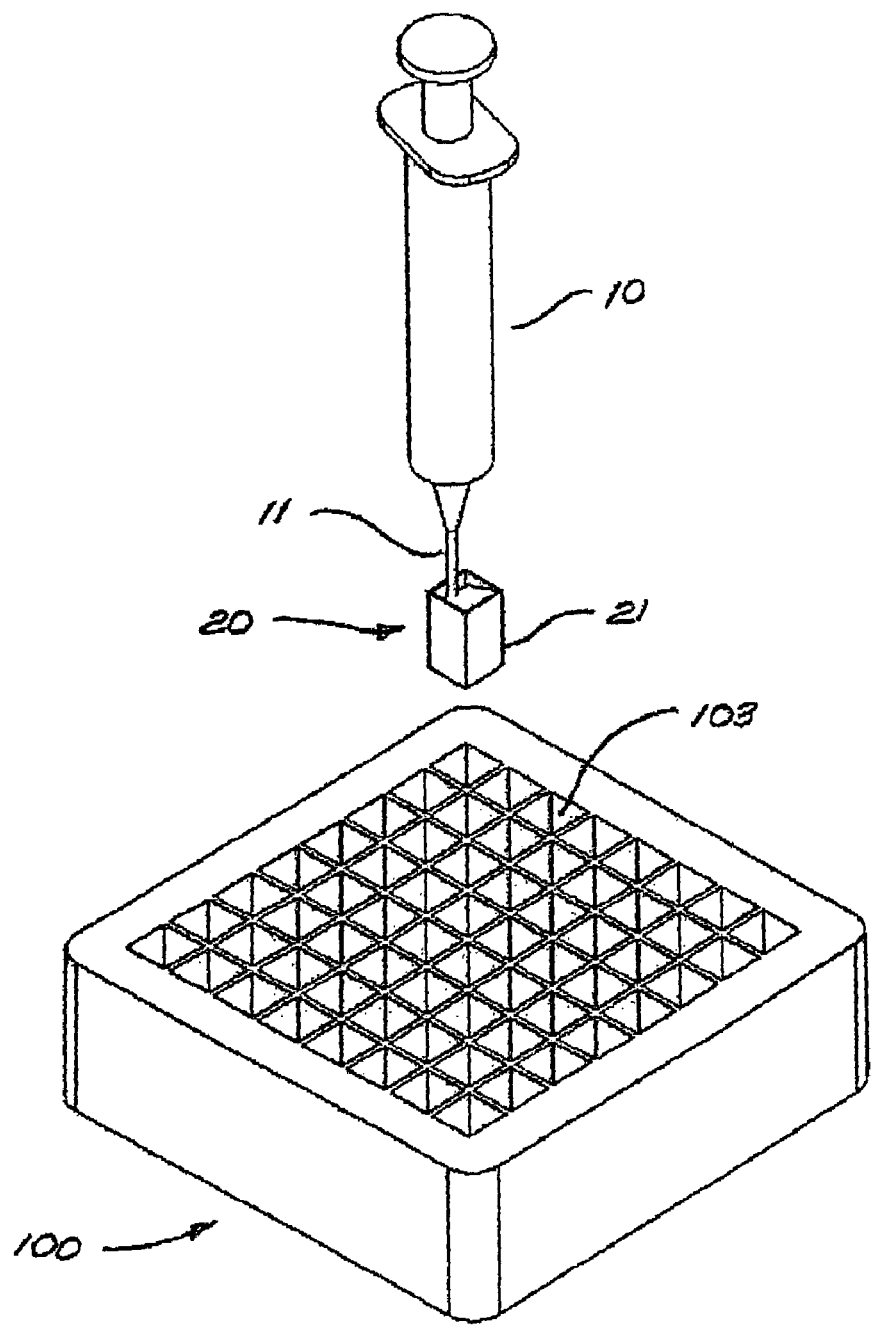
FIG. 19 shows a permanent needle capture element attached to a syringe needle in transport.

FIG. 15 illustrates a preferred holder for a plurality of capture members according to the present invention. FIG. 16 is a top perspective view of a syringe needle being placed into a capture member within a holding member. FIG. 17 is a top perspective view of a syringe needle being withdrawn with a capture member from within a holding member. FIG. 18 is a perspective top view of the arrangement of components according to the present invention. FIG. 19 shows a permanent needle capture element attached to a syringe needle in transport.

Referring now to FIGS. 15-19 a holding member or tray 100 is shown comprising a base having a bottom 101, a top 102 and sides 104. The bottom 101 of the tray 100 can be weighted or fitted with an adhesive material configured to keep the tray 100 in place as it is used. The top 102 of the tray 100 can be configured with a plurality of recesses 103 that are sized and configured to hold a plurality of capture elements 20. The tray 100 can be constructed of an elastomeric material, and the like, that can be formulated to provide a light holding force to the capture elements 20 when they are nested into the recesses 103.

An additional embodiment contemplates the use of rigid or flexible thermoplastics or other recycled materials, and the like. The tray 100 can be injection molded, vacuum formed, extruded or compression molded, and the like. The tray 100 provides a high density arrangement for the capture elements 20 with very little distance between the elements 20. The high density arrangement can decrease any opportunity to miss a capture element 20 when attempting to pick up a capture element 20. A typical wall 105 thickness between recesses can range between approximately 0.005" to approximately 0.025".

Referring now to FIGS. 15-19 a syringe 10 with a used or contaminated needle 11 can be aimed randomly at any of the capture elements 20 arranged within the holding tray 100 and moved forward until the needle 11 engages an end flap 24, 25 of one of the capture elements 20. It can then be pushed into the capture element 20 until it is fully engaged within the capture element 20. The syringe 10, captured needle 11 and capture element 20 can then be removed from the holding tray 100 and recapped or discarded.

Figure 20:
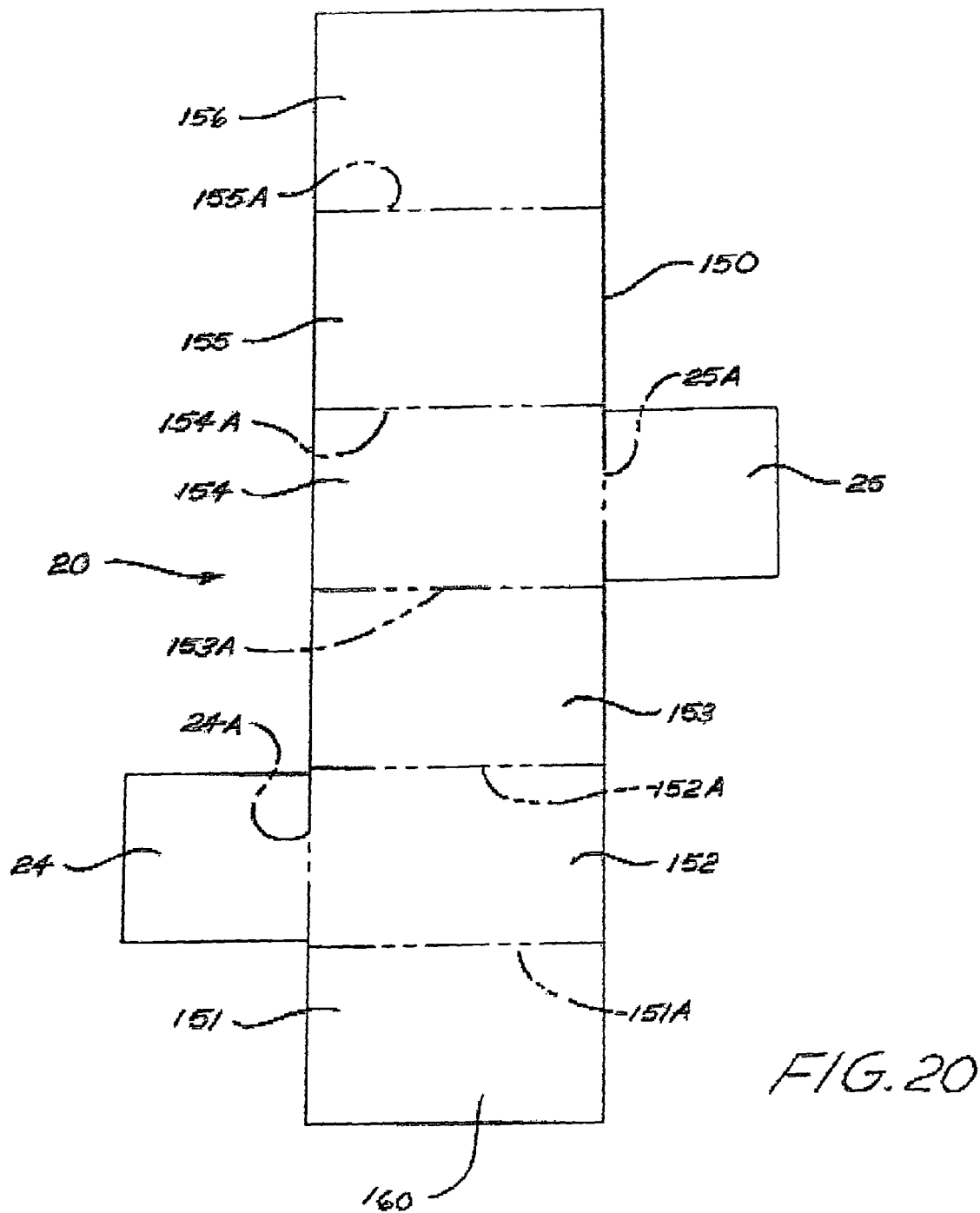
FIG. 20 illustrates a preferred method of construction for a capture element according to the present invention comprising a foldable flat-form.
Figure 21:
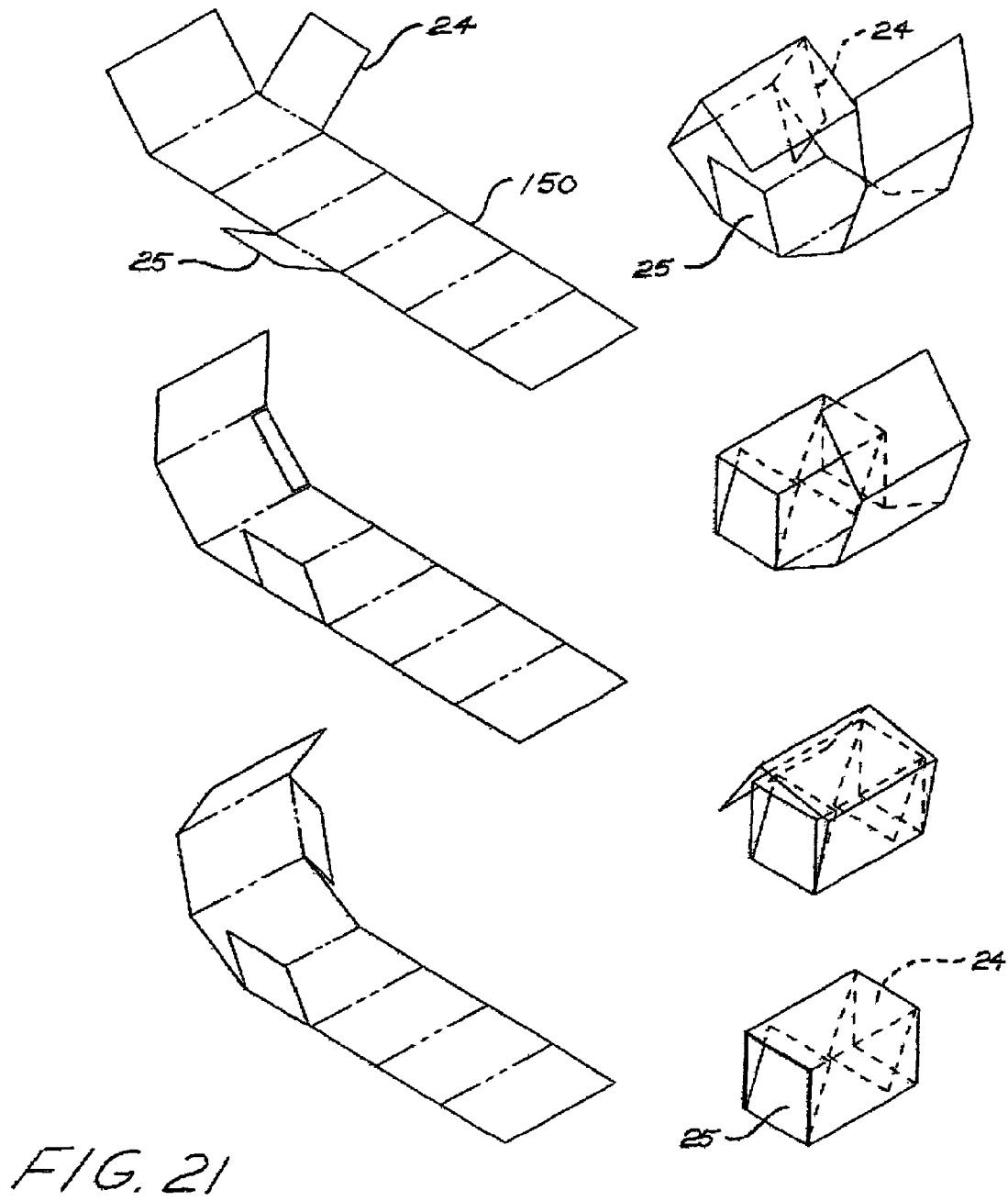
FIG. 21 illustrates a series of seven sequential folding operations that may comprise a preferred construction method having hidden lines.
Figure 22:
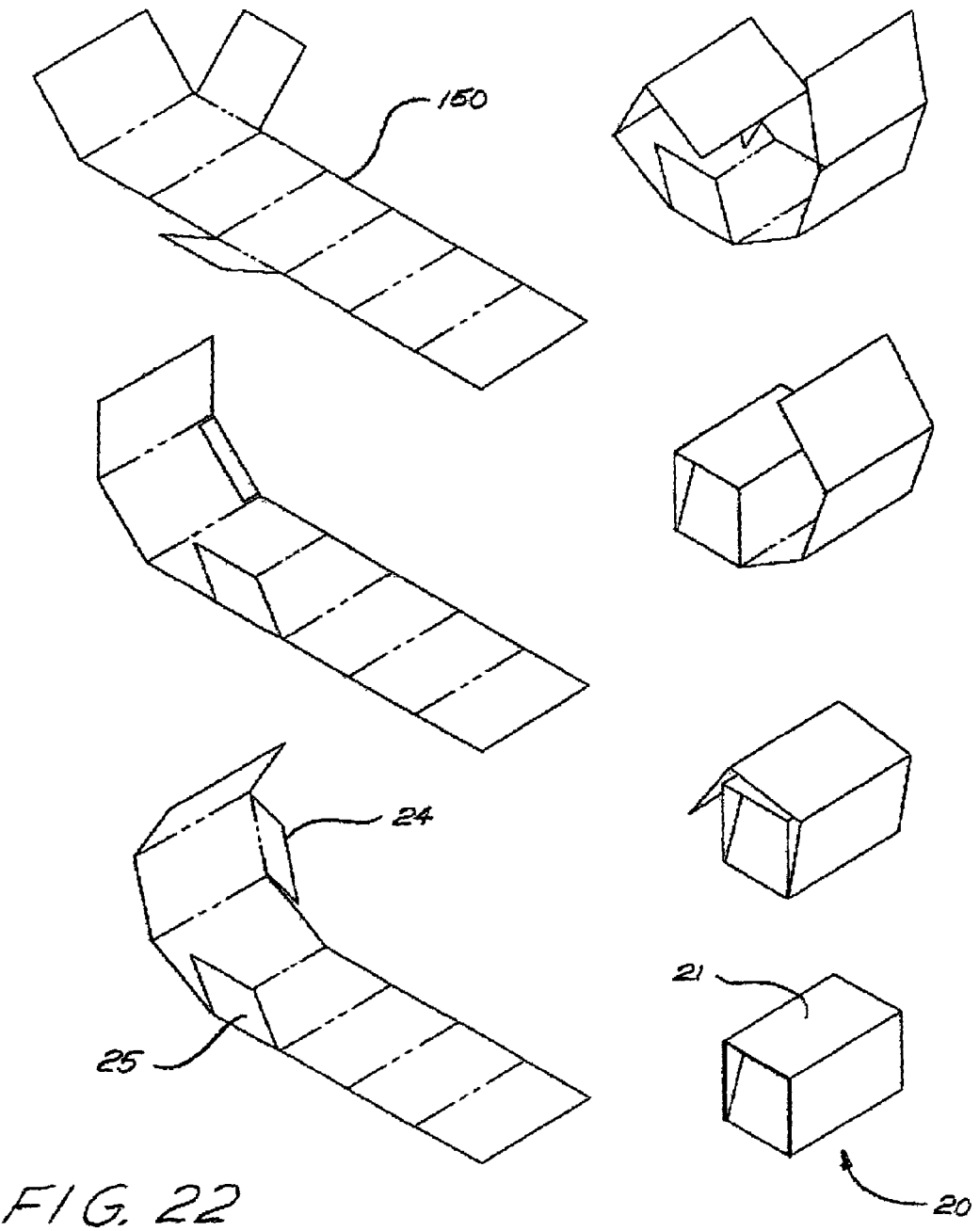
FIG. 22 illustrates a series of seven sequential folding operations that may comprise a preferred construction method without hidden lines for clarity.
Figure 23:
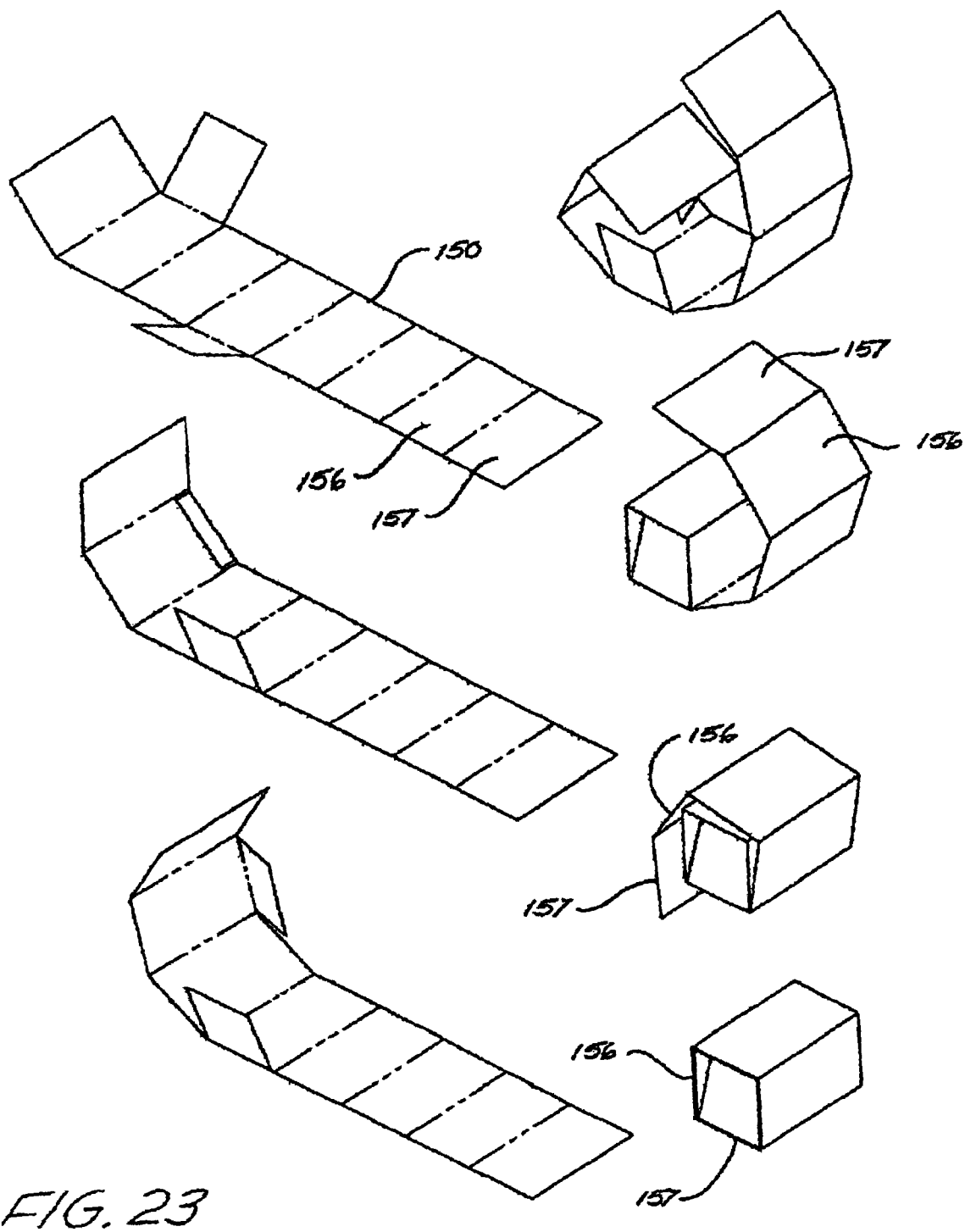
FIG. 23 illustrates a second preferred embodiment of the capture element in series of nine sequential folding operations.

FIG. 20 illustrates a preferred method of construction for a capture element according to the present invention comprising a foldable flat-form. FIG. 21 illustrates a series of seven sequential folding operations that may comprise a preferred construction method having hidden lines. FIG. 22 illustrates a series of seven sequential folding operations that may comprise a preferred construction method without hidden lines for clarity. FIG. 23 illustrates a second preferred embodiment of the capture element in series of nine sequential folding operations.

Referring to FIGS. 20-23 another preferred embodiment of the capture element 20 of the present invention can comprises a folded metal channel 21 having hinged end portions 24, 25. A preferred construction method can comprise a flat form 150 (FIG. 20) that is sized and configured to be foldable into a channel 21 with hinged end portions 24, 25. Preferably, the surface 160 that forms the inside of the channel 20 can be treated to increase traction upon an object in contact with the inside wall surfaces 27, 31 of the channel 21. The treatment can include but is not limited to acid etching, mechanical etching, sandblasting, embossing, stamping, and the like.

The first section 151 can be folded along a fold-line 151A over the second section 152 which is subsequently folded along a fold-line 152A over the third section 153 and so-on to form a substantially square elongate channel 21. A first end flap 24 can be folded inwardly to a preferred inward acute angle. Next, the shaped filler or resilient material 50 can be inserted within the channel 21 and the second end flap 25 can be folded inwardly to a preferred acute angle.

Depending upon construction preferences, the elongate channel 21 of the capture element 20 can comprise various numbers of overlapping, folded sections 151 through 156+. For instance, five or six overlapping sections 151+, and the like can be sufficient if the wall sections are adequately attached by weld or bond, and the like. Additionally if greater wall strength is required, seven, eight or more folded sections 151+ can also be used.

Figure 24:
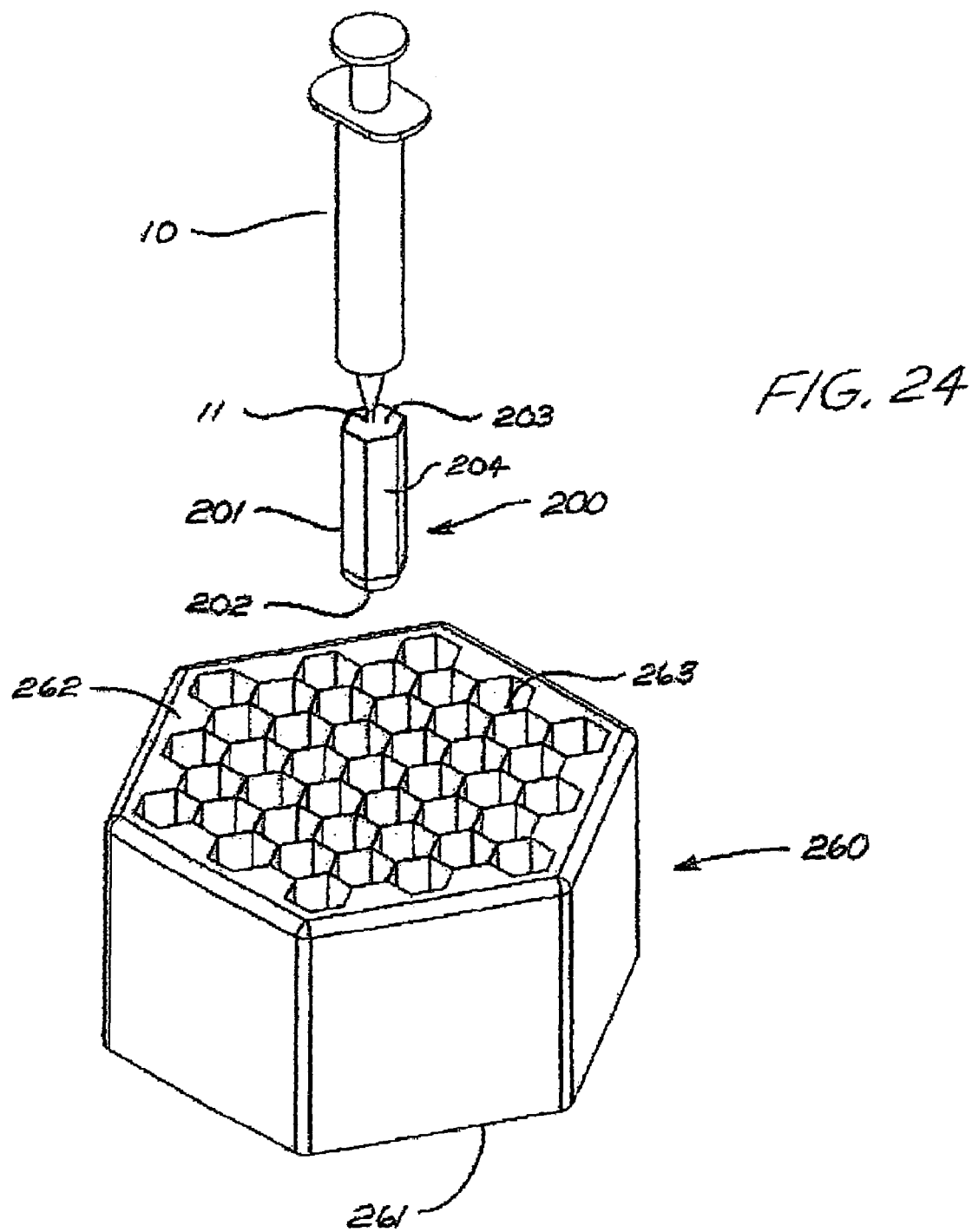
FIG. 24 is a perspective view of an alternate embodiment of the present invention comprising a chemically activated capture member.
Figure 25:
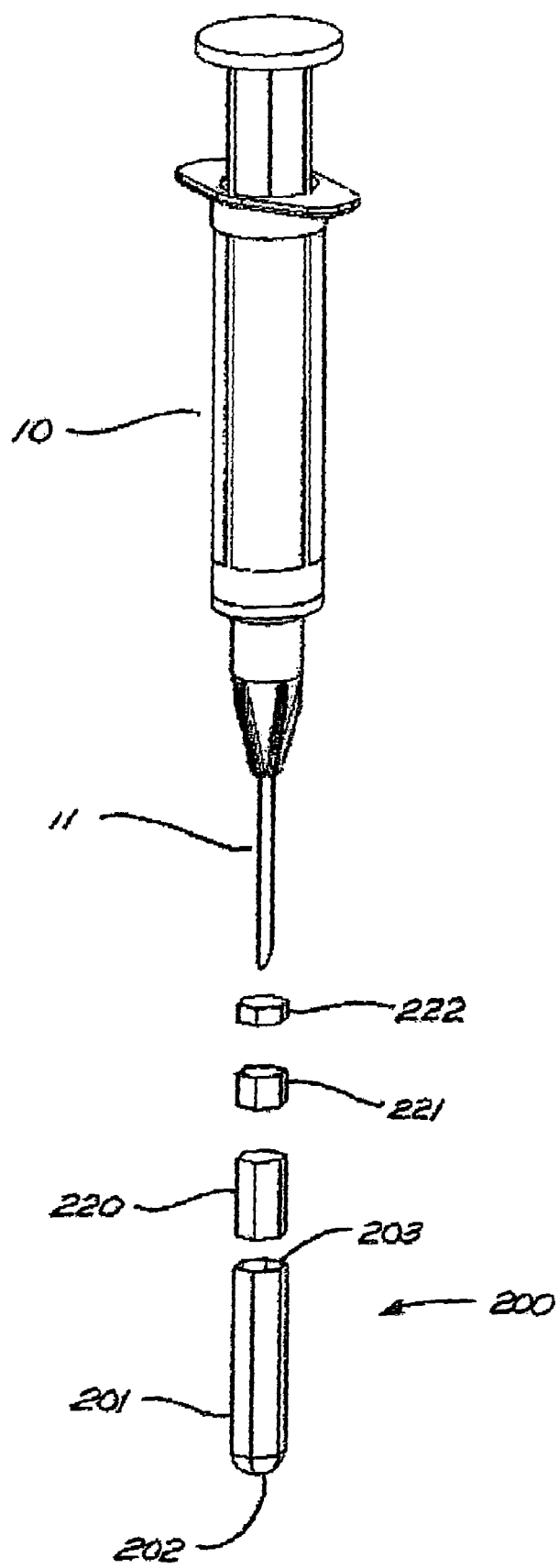
FIG. 25 is an exploded view of the individual elements of the capture member.
Figure 26:
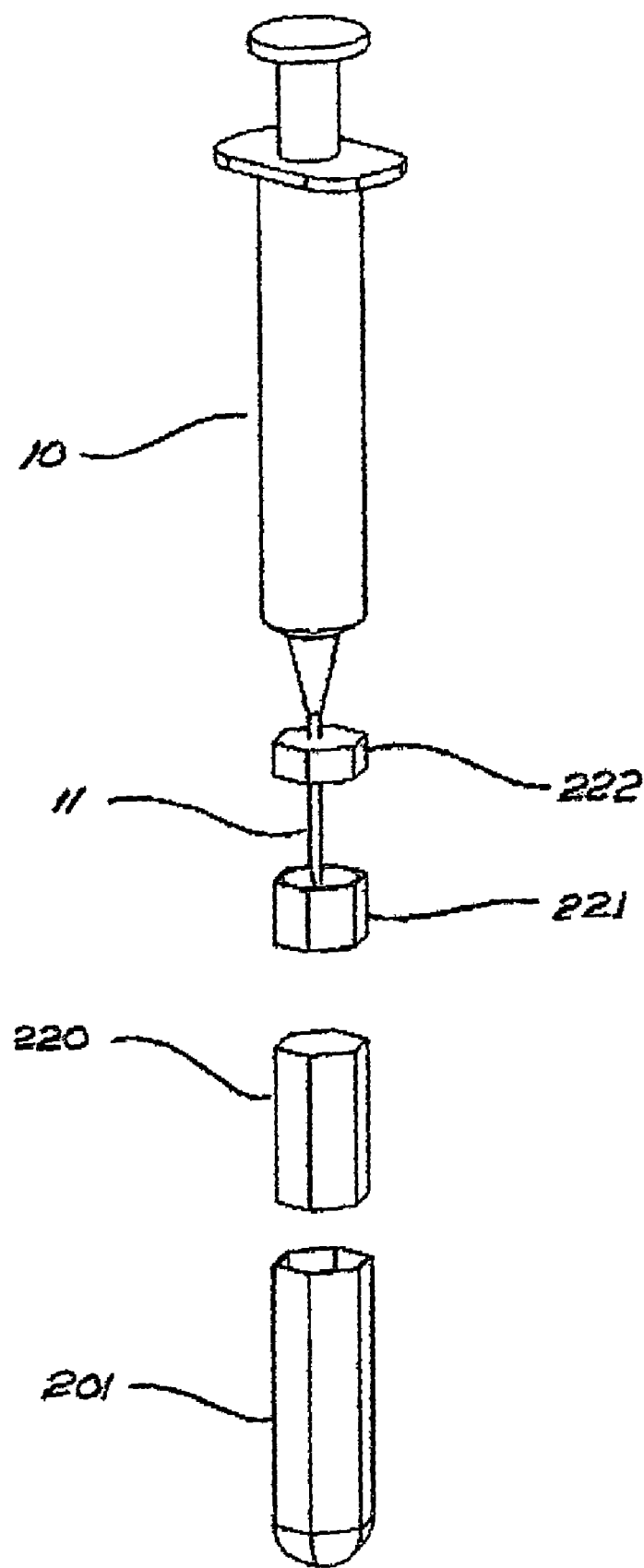
FIG. 26 is an exploded view of the individual elements of the capture member during the penetrating of a syringe needle.
Figure 27:
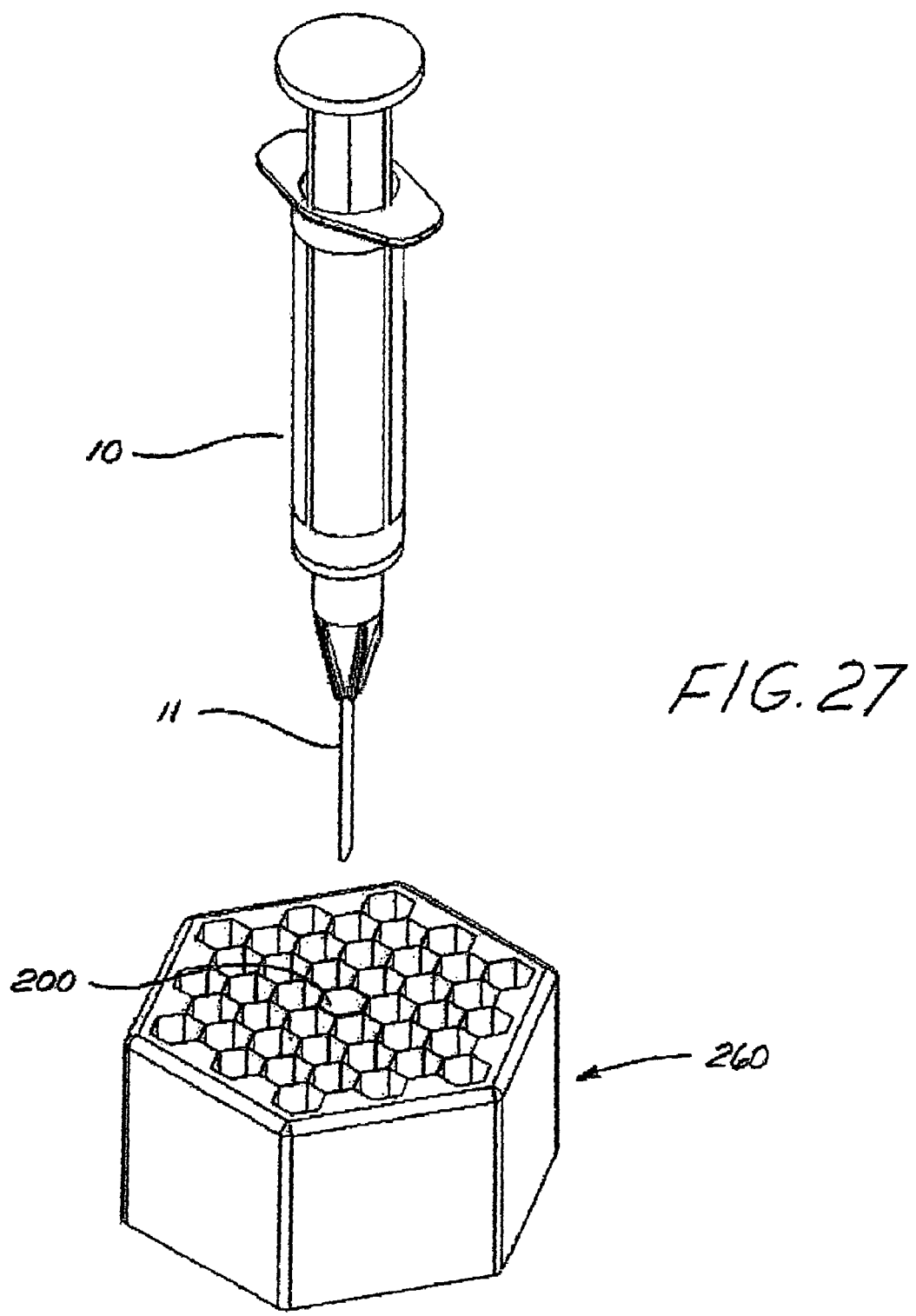
FIG. 27 shows the chemically activated capture member within a holding tray.
Figure 28:
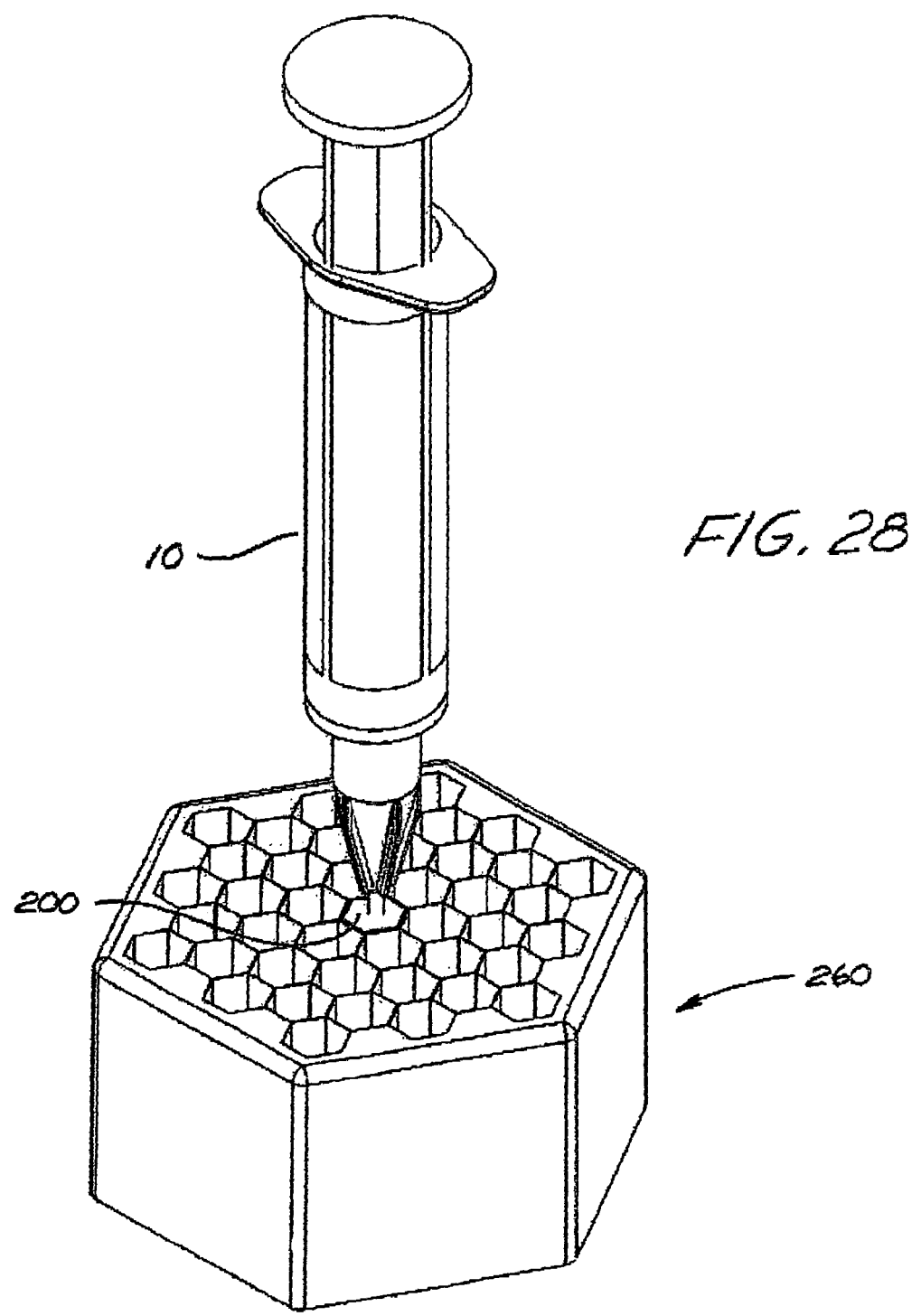
FIG. 28 illustrates a syringe needle being inserted into a chemically activated capture member.
Figure 29:
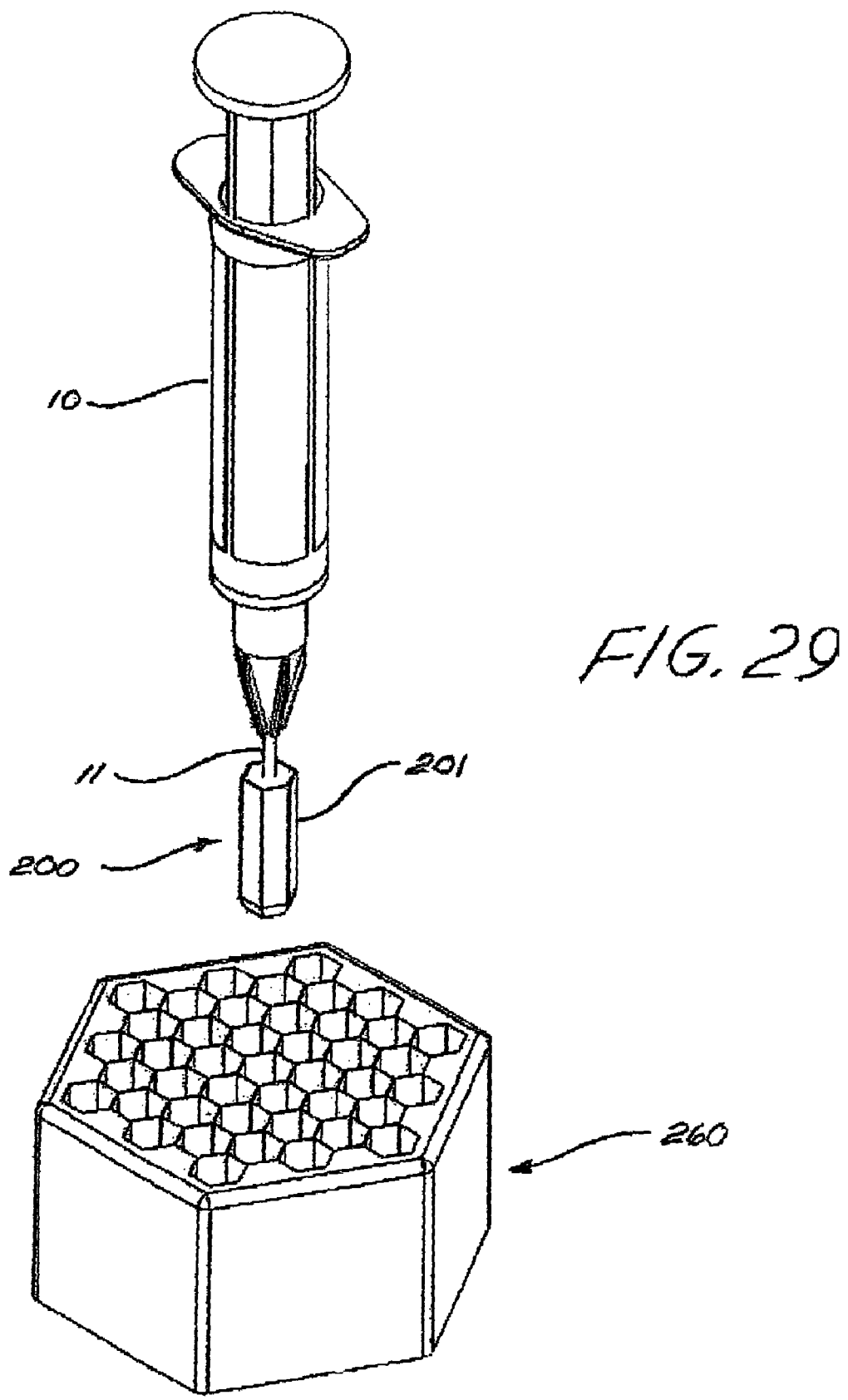
FIG. 29 illustrates a syringe needle permanently captured within a chemically activated capture member as it is removed from a holding tray for transport or disposal.

FIG. 24 is a perspective view of an alternate embodiment of the present invention comprising a chemically activated capture member. FIG. 25 is an exploded view of the individual elements of the capture member. FIG. 26 is an exploded view of the individual elements of the capture member during the penetrating of a syringe needle. FIG. 27 shows the chemically activated capture member within a holding tray. FIG. 28 illustrates a syringe needle being inserted into a chemically activated capture member. FIG. 29 illustrates a syringe needle permanently captured within a chemically activated capture member as it is removed from a holding tray for transport or disposal.

Referring now to FIGS. 24-29 another preferred embodiment of the present invention can comprise a capture element 200 sized and configured to permanently hold an inserted needle 11 or other sharp object. The capture element 200 can comprise an elongate channel 201 having a wall 204, a closed first end 202 and an open second end 203.

The channel 201 can be cylindrical, square, hexagonal or the like. A preferred embodiment can comprise a hexagonal channel 201 so that, when arranged in a holding member or tray 260, there is a great packing density, somewhat like a beehive. The channel 201 can be constructed of a material such as but not limited to rigid plastic, glass or metal, and the like, and can be sized and configured to nest into the recesses 263 of a holding member or tray 260.

The capture element 200 channel 201 can be filled with a plurality of materials that cooperate to permanently capture a needle 11 or sharp object within the channel 201 of the capture element 200. The materials used to fill the channel 201 can include but is not limited to chemicals that can react to each other on contact, chemicals that react to moisture, chemicals that cure on contact with air or chemicals that react to dispersion within one or more of the other materials within the channel 201.

The activation of the chemical materials within the channel 201 can be initiated by the penetration of needle 11 or other sharp object into the materials within the channel 201 of the capture element 200. An example of a combination of materials comprising a preferred embodiment can include a first, distal material 220 of natural cotton or other dispersing material, a second material 221 consisting of a penetrable sealed packet containing cyanoacrylate of very low viscosity (approximately 5 to approximately 15 cp (centipoises)) and an elastomeric entry seal 222.

In use, a moist, needle 11 can be introduced into the capture element 200, it first pierces and ruptures the sealed packet 221 and subsequently allows the supply of cyanoacrylate to wick into the cotton or dispersing material 220. There can be a nearly instant reaction in this environment so that the needle 11, cotton or dispersing material 220 and channel 201 are bonded together. Additional embodiments can include but is not limited to two-part epoxies or other adhesives, and the like, that can react upon penetration of a needle, introduction of air or presence of moisture.

FIG. 30 is an exploded view of an alternate embodiment of a binding capture element with a plastic shell. FIG. 31 illustrates an assembled alternate embodiment of a binding capture element with a plastic shell. FIG. 32 illustrates an assembled alternate embodiment of a binding capture element with a plastic shell with a needle approaching the open end. FIG. 33 illustrates an assembled alternate embodiment of a binding capture element with a plastic shell with a needle within the channel. FIG. 34 illustrates further alternate embodiment illustrating an alternate profile.

Referring to FIGS. 30-34 the needle capture element 20 can comprise a first external, elongate shell 300 having a proximal open end 304 and a distal closed end 302 and may be made of plastic, metal or the like. The shell 300 can be sized and configured to receive and hold a metal capture form 320 comprising a channel 321 having, at least a first hinged end flap 324. The end flap 324 can be sized and configured to allow a needle 11 to be inserted into the channel 321 but to bind against an inserted needle 11 when said needle 11 is moved proximally. It can be seen that there can be alternate shell and channel profiles that comprise embodiments of the present invention. The capture element 20 can have a geometrical shape such as but limited to being square, rectangular, hexagonal, octagonal, triangular, round, combinations thereof, and the like.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A needle capture device comprising:
    an elongate metal channel having a first hinged end flap extending from a first channel wall, where said first end flap is sized and configured to allow a needle to pass into said channel in a first direction, and where said end flap binds upon said needle when a force is applied to move said needle in a second direction; and
    a second hinged end flap extending from a second, opposing channel wall, where said second end flap is sized and configured to allow a needle to pass into said channel in said second direction, and where said second end flap binds upon said needle when a force is applied to move said needle in said first direction, and where the hinged portions of the end flaps are arranged so that a needle extending through a first end flap is forced into the folded hinge point portion of the second end flap, and where the hinged portions of the end flaps are arranged so that a needle extending through a second end flap is forced into the folded hinge point portion of the first end flap.

* * * * *